US009994865B2

(12) United States Patent
Fisher et al.

(10) Patent No.: US 9,994,865 B2
(45) Date of Patent: Jun. 12, 2018

(54) *PEG*-PROM MEDIATED SURFACE EXPRESSION OF AVIDIN/STREPTAVIDIN

(71) Applicants: The Johns Hopkins University, Baltimore, MD (US); Virginia Commonwealth University, Richmond, VA (US)

(72) Inventors: Paul B. Fisher, Richmond, VA (US); Swadesh K. Das, Richmond, VA (US); Mitchell E. Menezes, Richmond, VA (US); Devanand Sarkar, Richmond, VA (US); Martin G. Pomper, Baltimore, MD (US)

(73) Assignees: The Johns Hopkins University, Baltimore, MD (US); Virginia Commonwealth University, Richmond, VA (US)

( * ) Notice: Subject to any disclaimer, the term of this patent is extended or adjusted under 35 U.S.C. 154(b) by 0 days. days.

(21) Appl. No.: 14/895,125

(22) PCT Filed: Jun. 4, 2014

(86) PCT No.: PCT/US2014/040913
§ 371 (c)(1),
(2) Date: Dec. 1, 2015

(87) PCT Pub. No.: WO2014/197599
PCT Pub. Date: Dec. 11, 2014

(65) Prior Publication Data
US 2016/0108429 A1      Apr. 21, 2016

Related U.S. Application Data

(60) Provisional application No. 61/830,955, filed on Jun. 4, 2013.

(51) Int. Cl.
| | | |
|---|---|---|
| *A61K 48/00* | (2006.01) |
| *C12N 15/85* | (2006.01) |
| *C12N 15/64* | (2006.01) |
| *C07K 14/47* | (2006.01) |
| *G01N 33/50* | (2006.01) |
| *G01N 33/574* | (2006.01) |
| *A61K 38/16* | (2006.01) |
| *A61K 38/17* | (2006.01) |
| *A61K 38/20* | (2006.01) |
| *A61K 41/00* | (2006.01) |
| *A61K 49/00* | (2006.01) |
| *A61N 7/00* | (2006.01) |
| *C07K 14/36* | (2006.01) |
| *C07K 14/465* | (2006.01) |
| *C07K 14/54* | (2006.01) |
| *C12N 7/00* | (2006.01) |
| *C12N 15/86* | (2006.01) |
| *C12N 15/62* | (2006.01) |

| *B82Y 5/00* | (2011.01) |
| *B82Y 15/00* | (2011.01) |

(52) U.S. Cl.
CPC ............ *C12N 15/85* (2013.01); *A61K 38/164* (2013.01); *A61K 38/1703* (2013.01); *A61K 38/20* (2013.01); *A61K 41/0028* (2013.01); *A61K 48/0058* (2013.01); *A61K 48/0075* (2013.01); *A61K 49/00* (2013.01); *A61N 7/00* (2013.01); *C07K 14/36* (2013.01); *C07K 14/465* (2013.01); *C07K 14/47* (2013.01); *C07K 14/54* (2013.01); *C12N 7/00* (2013.01); *C12N 15/625* (2013.01); *C12N 15/64* (2013.01); *C12N 15/86* (2013.01); *G01N 33/50* (2013.01); *G01N 33/574* (2013.01); *A61K 48/00* (2013.01); *A61N 2007/0039* (2013.01); *B82Y 5/00* (2013.01); *B82Y 15/00* (2013.01); *C07K 2319/02* (2013.01); *C07K 2319/03* (2013.01); *C07K 2319/035* (2013.01); *C12N 2710/10043* (2013.01); *C12N 2799/02* (2013.01); *C12N 2799/022* (2013.01); *C12N 2800/22* (2013.01); *C12N 2810/855* (2013.01); *C12N 2830/002* (2013.01); *C12N 2830/008* (2013.01)

(58) Field of Classification Search
None
See application file for complete search history.

(56) References Cited

U.S. PATENT DOCUMENTS

| 4,405,712 A | 9/1983 | Vande Woude et al. |
| 4,650,764 A | 3/1987 | Temin et al. |
| 5,252,479 A | 10/1993 | Srivastava |
| 6,737,523 B1 | 5/2004 | Fisher et al. |
| 6,897,024 B2 | 5/2005 | Bussemakers et al. |

(Continued)

FOREIGN PATENT DOCUMENTS

| WO | WO-89/05345 | 6/1989 |
| WO | WO-90/06997 | 6/1990 |

(Continued)

OTHER PUBLICATIONS

Greco et al. Mole Therapy 2010;18:295-306.*

(Continued)

*Primary Examiner* — Janice Li
(74) *Attorney, Agent, or Firm* — Foley & Lardner LLP

(57) ABSTRACT

The presently disclosed subject matter relates to compositions and methods directed to cancer theranostic nucleic acid constructs that permit simultaneous cancer-specific viral replication, expression of a diagnostic gene product, and expression of a therapeutic gene.

18 Claims, 5 Drawing Sheets

(56) References Cited

U.S. PATENT DOCUMENTS

| | | | |
|---|---|---|---|
| 7,247,297 | B2 | 7/2007 | Weichselbaum et al. |
| 7,321,030 | B2 | 1/2008 | Hamada |
| 7,364,727 | B2 | 4/2008 | Li et al. |
| 7,816,131 | B2 | 10/2010 | Hung et al. |
| 8,034,914 | B2 | 10/2011 | Hochberg |
| 2002/0162134 | A1* | 10/2002 | Baguisi .............. A01K 67/0275 800/19 |
| 2005/0048578 | A1 | 3/2005 | Zhang |
| 2007/0092968 | A1 | 4/2007 | Ji et al. |
| 2008/0213220 | A1 | 9/2008 | Fisher et al. |
| 2009/0117177 | A1 | 5/2009 | Rapoport et al. |
| 2009/0311664 | A1 | 12/2009 | Fong et al. |
| 2012/0065251 | A1 | 3/2012 | Rosin-Arbesfeld et al. |
| 2016/0106866 | A1* | 4/2016 | Fisher ................ A61K 41/0033 424/1.11 |

FOREIGN PATENT DOCUMENTS

| | | |
|---|---|---|
| WO | WO-92/05266 | 4/1992 |
| WO | WO-92/07573 | 5/1992 |
| WO | WO-92/14829 | 9/1992 |
| WO | WO-2006/096815 | 9/2006 |
| WO | WO-2012/058522 | 5/2012 |

OTHER PUBLICATIONS

Sano et al. Biochem Biophy Res Comm 1991;176:571-7.*
Pedersen et al. Euro J Pharma and Biopharm 2006;62:155-162.*
Ogawa et al. Bioconjugate Chem. 2009;20: 147-154.*
Robbins et al, Pharmcol Ther 1998;80:35-47.*
Satyajit et al., "Sorting GPI-anchored proteins", Nat Rev Mol Cell Biol, vol. 5, No. 2, Feb. 1, 2004, pp. 110-120.
Search report issued on European Application 14808337, dated Dec. 12, 2016.
Berkner. "Development of adenovirus vectors for the expression of heterologous genes," Biotechniques 6: 616-626 (1988).
Blaese et al., "T Lymphocyte-Directed Gene Therapy for ADA-212 SCID: Initial Trial Results After 4 Years," Science 270: 475-479 (1995).
Blasberg et al., "Molecular-genetic imaging: current and future perspectives," J. Clin. Invest. vol. 111; No. 11; pp. 1620-1629; (2003).
Chen et al., "Reversal of streptozotocin-induced diabetes in rats by gene therapy with betacellulin and pancreatic duodenal homeobox-1," Gene Ther. 14(14): 1102-1110 (2007).
Cotten et al., "High-efficiency receptor-mediated delivery of small and large (48 kilobase gene constructs using the endosome-disruption activity of defective or chemically inactivated adenovirus particles," Proc. Natl. Acad. Sci. USA 89(13): 6094-6098 (1992).
Danos et al., "Safe and efficient generation of recombinant retroviruses with amphotropic and ecotropic host ranges," Proc. Natl. Acad. Sci. USA 85(17): 6460-6464 (1988).
Dash et al., "Apogossypol derivative Bi-97C1 (Sabutoclax) targeting Mcl-I sensitizes prostate cancer cells to mda-7/IL-24-mediated toxicity." Proc. Natl. Acad. Sci. USA 108: 8785-8790 (2011).
Dash et al., "Developing an effective gene therapy for prostate cancer: new technologies with potential to translate from the laboratory into the clinic," Discov Med 11: 46-56 (2011).
Donahue et al., "Reduction in SIV replication in rhesus macaques infused with autologous lymphocytes engineered with antiviral genes," Nature Medicine 4(2):181-186 (1998).
Doronin et al., "Tissue-Specific, Tumor-Selective, Replication-Competent Adenovirus Vector for Cancer Gene Therapy," J. Virol. 75(7): 3314-3324 (2001).
Freireich et al., "Quantitative comparison of toxicity of anticancer agents in mouse, rat, hamster, dog, monkey, and man," Cancer Chemother. Rep. 50(4): 219-44 (1966).
Freytag et al., "Phase I Trial of Replication-competent Adenovirus-mediated Suicide Gene Therapy Combined with IMRT for Prostate Cancer," Mol. Ther. 15(5): 10165-1023 (2007).
Fujii et al., "Ultrasound-Targeted Gene Delivery Induces Angiogenesis After a Myocardial Infarction in Mice," J. Am. Coll. Cardiovasc. Imaging 2: 869-879.
Geller et al., "A Defective HSV-1 Vector Expresses *Eschirichia coli* beta-galactosidase in Cultured Peripheral Neurons," Science 241: 1667-1669 (1988).
Gilad et al., "Artificial reporter gene providing MRI contrast based on proton exchange," Nature Biotechnology 25(2): 217-219 (2007).
Gilad et al., "MRI Reporter Genes," J. Nucl. Med. 49(12): 1905-1908 (2008).
Goldman et al., "Lentiviral Vectors for Gene Therapy of Cystic Fibrosis," Human Gene Therapy 10: 2261-2268 (1997).
Gotoh et al., "Cell-surface streptavidin fusion protein for rapid selection of transfected mammalian cells," Gene 389(2): 146-153 (2007).
Graham et al., "Manipulation of Adenovirus Vectors," Methods in Mol. Biol.: Gene Transfer and Expression Protocols 7: 109-127 (1991).
Greelish et al., "Stable restoration of the sarcoglycan complex in dystrophic muscle perfused with histamine and a recombinant adeno-associated viral vector," Nature Med. 5:439-443 (1999).
Hallenbeck et al., "A Novel Tumor-Specific Replication-Restricted Adenoviral Vector for Gene Therapy of Hepatocellular Carcinoma," Human Gene Therapy 10(10): 1721-1733 (1999).
Herzog et al., "Long-term correction of canine hemophilia B by gene transfer of blood coagulation factor IX mediated by adeno-associated viral vector," Nature Medicine 5(1): 56-63 (1999).
Hobbs et al., "A nephron-based model of the kidneys for macro-to-micro alpha-particle dosimetry," Phys. Med. Biol. 57(13): 4403-4424 (2012).
International Preliminary Report on Patentability for PCT/US2014/040913, dated Dec. 8, 2015.
International Search Report on PCT/US2014/040913, dated Oct. 27, 2014.
Kafri et al., "Sustained expression of genes delivered directly into liver and muscle by lentiviral vectors," Nature Genetics 17(3): 314-317 (1997).
Kishimoto et al., "In vivo imaging of lymph node metastasis with telomerase-specific replication-selective adenovirus," Nature Medicine 12(10): 1312-1219 (2006).
Kurihara et al., "Selectivity of a replication-competent adenovirus for human breast carcinoma cells expressing the MUC1 antigen," J. Clin. Invest. 106: 763-771 (2000).
Laitinen et al., "Brave new (strept)avidins in biotechnology," Trends Biotech 25: 269-277 (2007).
Lee et al., "Selective Activation of Ceruloplasmin Promoter in Ovarian Tumors: Potential Use for Gene Therapy," Cancer Res. 64(5): 1788 (2004).
Li et al., "Assessment of Recombinant Adenoviral Vectors for Hepatic Gene Therapy," Human Gene Therapy 4:403-409 (1993).
Mocarski et al "Viral Vectors." Gluzman and Hughes (eds.). Cold Spring Harbor Laboratory, Cold Spring Harbor, N.U., 1988, pp. 78-84.
Onodera et al., "Development of Improved Adenosine Deaminase Retroviral Vectors," J. Virol. 72(3):1769-1774 (1998).
Padmanabhan et al., "Visualization of Telomerase Reverse Transcriptase (hTERT) Promoter Activity Using a Trimodality Fusion Reporter Construct," J. Nucl. Med. 47(2): 270-277 (2006).
Piccini et al., "Vaccinia virus as an expression vector," Meth. Enzymology 153: 545-563 (1987).
Qiu et al., "Primary structure of c-kit: relationship with the CSF-1/PDGF receptor kinase family—oncogenic activation of v-kit involves deletion of extracellular domain and C terminus," EMBO J. 7(4): 1003-1011 (1988).
Rodriguez et al., "Prostate Attenuated Replication Competent Adenovirus (ARCA) CN706: A Selective Cytotoxic for Prostate-specific Antigen-positive Prostate Cancer Cells," Cancer Res. 57(13): 2559-2563 (1997).
Sambrook et al, "Molecular Cloning. A Laboratory Manual", 2d ed., Cold Spring Harbor Laboratory, New York (1989).
Shackleford et al., "Construction of a clonable, infectious, and tumorigenic mouse mammary tumor virus provirus and a derivative genetic vector," Proc. Natl. Acad. Sci. USA 85: 9655-9659 (1988).

(56) References Cited

OTHER PUBLICATIONS

Snyder et al., "Correction of hemophilia B in canine and murine models using recombinant adeno-associated viral vectors," Nature Medicine 5(1): 64-70 (1999).

Uhrbom et al., "Dissecting tumor maintenance requirements using bioluminescence imaging of cell proliferation in a mouse glioma model," Nature Medicine 10(11): 1257-1260 (2004).

Venkatesan et., "The potential of celecoxib-loaded hydroxyapatite-chitosan nanocomposite for the treatment of colon cancer," Biomaterials 32(15): 3794-3806 (2011).

Wang et al., "Nucleotide sequences of three H-2K and three H-2D complementary DNA clones coding mouse class I MHC heavy chain proteins," Ann. Transplant. 1(3): 26-31 (1996).

Wang et al., "Sustained correction of bleeding disorder in hemophilia B mice by gene therapy," Proc. Natl. Acad. Sci. USA 96: 3906-3910 (1999).

Yaghoubi et al., "Noninvasive detection of therapeutic cytolytic T cells with 18F-FHBG PET in a patient with glioma," Nat. Clin. Pract. Oncol. 6: 53-58 (2009).

Zabner et al., "Safety and efficacy of repetitive adenovirus-mediated transfer of CFTR cDNA to airway epithelia of primates and cotton rats," Nature Genetics 6:75-83 (1994).

Zhang et al., "ABCG2/BCRP Expression Modulates d-Luciferin-Based Bioluminescence Imaging," Cancer Research 67: 9389-9397 (2007).

\* cited by examiner

PC3 cells transfected with Streptavidin

US 9,994,865 B2

SEQUENCE LISTING

```
<160> NUMBER OF SEQ ID NOS: 18

<210> SEQ ID NO 1
<211> LENGTH: 25
<212> TYPE: DNA
<213> ORGANISM: Artificial Sequence
<220> FEATURE:
<223> OTHER INFORMATION: PCR primer

<400> SEQUENCE: 1
ggactagtgc ctcgactgtg ccttc                                           25

<210> SEQ ID NO 2
<211> LENGTH: 25
<212> TYPE: DNA
<213> ORGANISM: Artificial Sequence
<220> FEATURE:
<223> OTHER INFORMATION: PCR primer

<400> SEQUENCE: 2
cggggtacct ccccagcatg cctgc                                           25

<210> SEQ ID NO 3
<211> LENGTH: 78
<212> TYPE: DNA
<213> ORGANISM: Artificial Sequence
<220> FEATURE:
<223> OTHER INFORMATION: annealing oligonucleotide

<400> SEQUENCE: 3
gatccctgtt cacgccgctg ctcattggct ttgtggtcgc agctggcgcg atggggatca    60
ttgtgatggt gctctaaa                                                   78

<210> SEQ ID NO 4
<211> LENGTH: 78
<212> TYPE: DNA
<213> ORGANISM: Artificial Sequence
<220> FEATURE:
<223> OTHER INFORMATION: annealing oligonucleotide

<400> SEQUENCE: 4
ctagtttaga gcaccatcac aatgatcccc atcgcgccag ctgcgaccac aaagccaatg    60
agcagcggcg tgaacagg                                                   78

<210> SEQ ID NO 5
<211> LENGTH: 99
<212> TYPE: DNA
<213> ORGANISM: Artificial Sequence
<220> FEATURE:
<223> OTHER INFORMATION: annealing oligonucleotide

<400> SEQUENCE: 5
gatccgagcc tcctccatcc actgtctcca acacggtaat cattgctgtt ctggttgtcc    60
```

```
ttggagctgc aatagtcact ggagctgtgg tggcttaaa                              99

<210> SEQ ID NO 6
<211> LENGTH: 99
<212> TYPE: DNA
<213> ORGANISM: Artificial Sequence
<220> FEATURE:
<223> OTHER INFORMATION: annealing oligonucleotide

<400> SEQUENCE: 6
ctagtttaag ccaccacagc tccagtgact attgcagctc caaggacaac cagaacagca       60
atgattaccg tgttggagac agtggatgga ggaggctcg                             99

<210> SEQ ID NO 7
<211> LENGTH: 79
<212> TYPE: DNA
<213> ORGANISM: Artificial Sequence
<220> FEATURE:
<223> OTHER INFORMATION: annealing oligonucleotide

<400> SEQUENCE: 7
tcgacgccgc catgagaggc gctcgcggcg cctgggatct gctctgcgtc ctgttggtcc       60
tgctccgtgg ccagggggcc                                                  79

<210> SEQ ID NO 8
<211> LENGTH: 71
<212> TYPE: DNA
<213> ORGANISM: Artificial Sequence
<220> FEATURE:
<223> OTHER INFORMATION: annealing oligonucleotide

<400> SEQUENCE: 8
cctggccacg gagcaggacc aacaggacgc agagcagatc ccaggcgccg cgagcgcctc       60
tcatggcggc g                                                           71

<210> SEQ ID NO 9
<211> LENGTH: 79
<212> TYPE: DNA
<213> ORGANISM: Artificial Sequence
<220> FEATURE:
<223> OTHER INFORMATION: annealing oligonucleotide

<400> SEQUENCE: 9
tcgacgccgc catggcaccc tgcatgctgc tcctgctgtt ggcggccgcc ctggccccga       60
ctcagacccg cgcggggcc                                                   79

<210> SEQ ID NO 10
<211> LENGTH: 71
<212> TYPE: DNA
<213> ORGANISM: Artificial Sequence
<220> FEATURE:
<223> OTHER INFORMATION: annealing oligonucleotide

<400> SEQUENCE: 10
ccgcgcgggt ctgagtcggg gccagggcgg ccgccaacag caggagcagc atgcagggtg       60
ccatggcggc g                                                           71

<210> SEQ ID NO 11
<211> LENGTH: 33
<212> TYPE: DNA
<213> ORGANISM: Artificial Sequence
<220> FEATURE:
<223> OTHER INFORMATION: PCR primer
```

<400> SEQUENCE: 11
cacggggccc gccgccagaa agtgctcgct gac                    33

<210> SEQ ID NO 12
<211> LENGTH: 31
<212> TYPE: DNA
<213> ORGANISM: Artificial Sequence
<220> FEATURE:
<223> OTHER INFORMATION: PCR primer

<400> SEQUENCE: 12
atcgcggatc cctccttctg tgtgcgcagg c                      31

<210> SEQ ID NO 13
<211> LENGTH: 31
<212> TYPE: DNA
<213> ORGANISM: Artificial Sequence
<220> FEATURE:
<223> OTHER INFORMATION: PCR primer

<400> SEQUENCE: 13
cacggggccc gccgccatgg accctccaa g                       31

<210> SEQ ID NO 14
<211> LENGTH: 29
<212> TYPE: DNA
<213> ORGANISM: Artificial Sequence
<220> FEATURE:
<223> OTHER INFORMATION: PCR primer

<400> SEQUENCE: 14
atcgcggatc cctgctgaac ggcgtcgag                         29

<210> SEQ ID NO 15
<211> LENGTH: 1253
<212> TYPE: DNA
<213> ORGANISM: Artificial Sequence
<220> FEATURE:
<223> OTHER INFORMATION: pPEG-H2K-avidin-BGHpolyA

<400> SEQUENCE: 15
gaaagagaaa gagaatggga cagcatgtga ctgcctgatg aagttggcgt gcttgctcaa      60
aagttctgcg agattgacgg ctctctggat ttgagccaag acacgcctg ggaagccacg      120 gtgacctcac aaggcccgga atctccgcga gaatttcagt gttgttttcc tctctccacc     180
tttctcaggg acttccgaaa ctccgcctct ccggtgacgt cagcatagcg ctgcgtcaga     240
ctataaactc ccgggtgatc gtgttggcgc agattgactc agttcgcagc ttgtggaaga     300
ttacatgcga gaccccgcgc gactccgcat ccctttgccg ggacagcctt tgcgacagcc     360
cgtgagacat cacgtccccg agcccacgc ctgagggcga catgaacgcg ctggccttga      420
gagcaatccg gacccacgat cgcttttggc aaaccgaacc ggaccgtcga cgccgccatg     480
gcaccctgca tgctgctcct gctgttggcg gccgccctgg ccccgactca gacccgcgcg     540
gggcccgccg ccagaaagtg ctcgctgact gggaaatgga ccaacgatct gggctccaac     600
atgaccatcg gggctgtgaa cagcagaggt gaattcacag gcacctacat cacagccgta     660
acagccacat caaatgagat caaagagtca ccactgcatg gacacaaaaa caccatcaac     720
aagaggaccc agcccacctt tggcttcacc gtcaattgga gttttcaga gtccaccact     780 gtcttcacgg gccagtgctt catagacagg aatgggaagg aggtcctgaa gaccatgtgg     840

| | |
|---|---|
| ctgctgcggt caagtgttaa tgacattggt gatgactgga aagctaccag ggtcggcatc | 900 |
| aacatcttca ctcgcctgcg cacacagaag gagggatccg agcctcctcc atccactgtc | 960 |
| tccaacacgg taatcattgc tgttctggtt gtccttggag ctgcaatagt cactggagct | 1020 |
| gtggtggctt aaactagtgc ctcgactgtg ccttctagtt gccagccatc tgttgtttgc | 1080 |
| ccctcccccg tgccttcctt gaccctggaa ggtgccactc ccactgtcct ttcctaataa | 1140 |
| aatgaggaaa ttgcatcgca ttgtctgagt aggtgtcatt ctattctggg ggtgggggtg | 1200 |
| gggcaggaca gcaagggggga ggattgggaa gacaatagca ggcatgctgg gga | 1253 |

<210> SEQ ID NO 16
<211> LENGTH: 1232
<212> TYPE: DNA
<213> ORGANISM: Artificial Sequence
<220> FEATURE:
<223> OTHER INFORMATION: pPEG-cKitsig-avidin-BGHpA

<400> SEQUENCE: 16

| | |
|---|---|
| gaaagagaaa gagaatggga cagcatgtga ctgcctgatg aagttggcgt gcttgctcaa | 60 |
| aagttctgcg agattgacgg ctctctggat ttgagccaag gacacgcctg ggaagccacg | 120 |
| gtgacctcac aaggcccgga atctccgcga gaatttcagt gttgttttcc tctctccacc | 180 |
| tttctcaggg acttccgaaa ctccgcctct ccggtgacgt cagcatagcg ctgcgtcaga | 240 |
| ctataaactc ccgggtgatc gtgttggcgc agattgactc agttcgcagc ttgtggaaga | 300 |
| ttacatgcga daccccgcgc gactccgcat ccctttgccg ggacagcctt tgcgacagcc | 360 |
| cgtgagacat cacgtccccg agccccacgc ctgagggcga catgaacgcg ctggccttga | 420 |
| gagcaatccg gacccacgat cgcttttggc aaaccgaacc ggaccgtcga cgccgccatg | 480 |
| agaggcgctc gcgcgcctg ggatctgctc tgcgtcctgt tggtcctgct ccgtggccag | 540 |
| gggcccgccg ccagaaagtg ctcgctgact gggaaatgga ccaacgatct gggctccaac | 600 |
| atgaccatcg gggctgtgaa cagcagaggt gaattcacag gcacctacat cacagccgta | 660 |
| acagccacat caaatgagat caaagagtca ccactgcatg gacacaaaa caccatcaac | 720 |
| aagaggaccc agcccacctt tggcttcacc gtcaattgga gttttcaga gtccaccact | 780 |
| gtcttcacgg gccagtgctt catagacagg aatgggaagg aggtcctgaa gaccatgtgg | 840 |
| ctgctgcggt caagtgttaa tgacattggt gatgactgga aagctaccag ggtcggcatc | 900 |
| aacatcttca ctcgcctgcg cacacagaag gagggatccc tgttcacgcc gttgctcatt | 960 |
| ggctttgtgg tcgcagctgg cgcgatgggg atcattgtga tggtgctcta aactagtgcc | 1020 |
| tcgactgtgc cttctagttg ccagccatct gttgtttgcc cctcccccgt gccttccttg | 1080 |
| accctggaag gtgccactcc cactgtcctt tcctaataaa atgaggaaat tgcatcgcat | 1140 |
| tgtctgagta ggtgtcattc tattctgggg ggtgggggtgg ggcaggacag caaggggggag | 1200 |
| gattgggaag acaatagcag gcatgctggg ga | 1232 |

<210> SEQ ID NO 17
<211> LENGTH: 1360
<212> TYPE: DNA
<213> ORGANISM: Artificial Sequence
<220> FEATURE:
<223> OTHER INFORMATION: pPEG-H2K-streptavidin-BGHpA

<400> SEQUENCE: 17

| | |
|---|---|
| gcggccgcga aagagaaaga gaatgggaca gcatgtgact gcctgatgaa gttggcgtgc | 60 |
| ttgctcaaaa gttctgcgag attgacggct ctctggattt gagccaagga cacgcctggg | 120 |

| | | |
|---|---|---|
| aagccacggt gacctcacaa ggcccggaat ctccgcgaga atttcagtgt tgttttcctc | 180 | |
| tctccacctt tctcagggac ttccgaaact ccgcctctcc ggtgacgtca gcatagcgct | 240 | |
| gcgtcagact ataaactccc gggtgatcgt gttggcgcag attgactcag ttcgcagctt | 300 | |
| gtggaagatt acatgcgaga ccccgcgcga ctccgcatcc ctttgccggg acagcctttg | 360 | |
| cgacagcccg tgagacatca cgtccccgag ccccacgcct gagggcgaca tgaacgcgct | 420 | |
| ggccttgaga gcaatccgga cccacgatcg cttttggcaa accgaaccgg accgtcgacg | 480 | |
| ccgccatggc accctgcatg ctgctcctgc tgttggcggc cgccctggcc ccgactcaga | 540 | |
| cccgcgcggg gcccgccgcc atggacccct ccaaggactc gaaggcccag gtctcggccg | 600 | |
| ccgaggccgg catcaccggc acctggtaca accagctcgg ctcgaccttc atcgtgaccg | 660 | |
| cgggcgccga cggcgccctg accggaacct acgagtcggc cgtcggcaac gccgagagcc | 720 | |
| gctacgtcct gaccggtcgt tacgacagcg ccccggccac cgacggcagc ggcaccgccc | 780 | |
| tcggttggac ggtggcctgg aagaataact accgcaacgc ccactccgcg accacgtgga | 840 | |
| gcggccagta cgtcggcggc gccgaggcga ggatcaacac ccagtggctg ctgacctccg | 900 | |
| gcaccaccga ggccaacgcc tggaagtcca cgctggtcgg ccacgacacc ttcaccaagg | 960 | |
| tgaagccgtc cgccgcctcc atcgacgcgg cgaagaaggc cggcgtcaac aacggcaacc | 1020 | |
| cgctcgacgc cgttcagcag ggatccgagc ctcctccatc cactgtctcc aacacggtaa | 1080 | |
| tcattgctgt tctggttgtc cttggagctg caatagtcac tggagctgtg gtggcttaaa | 1140 | |
| tcagtgcctc gactgtgcct tctagttgcc agccatctgt tgtttgcccc tcccccgtgc | 1200 | |
| cttccttgac cctggaaggt gccactccca ctgtcctttc ctaataaaat gaggaaattg | 1260 | |
| catcgcattg tctgagtagg tgtcattcta ttctgggggg tggggtgggg caggacagca | 1320 | |
| aggggaggga ttgggaagac aatagcaggc atgctgggga | 1360 | |

<210> SEQ ID NO 18
<211> LENGTH: 1331
<212> TYPE: DNA
<213> ORGANISM: Artificial Sequence
<220> FEATURE:
<223> OTHER INFORMATION: pPEG-cKit-streptavidin-BGHpA

<400> SEQUENCE: 18

| | | |
|---|---|---|
| gaaagagaaa gagaatggga cagcatgtga ctgcctgatg aagttggcgt gcttgctcaa | 60 | |
| aagttctgcg agattgacgg ctctctggat ttgagccaag dacacgcctg ggaagccacg | 120 | |
| gtgacctcac aaggcccgga atctccgcga gaatttcagt gttgttttcc tctctccacc | 180 | |
| tttctcaggg acttccgaaa ctccgcctct ccggtgacgt cagcatagcg ctgcgtcaga | 240 | |
| ctataaactc ccgggtgatc gtgttggcgc agattgactc agttcgcagc ttgtggaaga | 300 | |
| ttacatgcga gaccccgcgc gactccgcat ccctttgccg ggacagcctt tgcgacagcc | 360 | |
| cgtgagacat cacgtccccg agccccacgc ctgagggcga catgaacgcg ctggccttga | 420 | |
| gagcaatccg gacccacgat cgcttttggc aaaccgaacc ggaccgtcga cgccgccatg | 480 | |
| agaggcgctc gcgcgccctg ggatctgctc tgcgtcctgt tggtcctgct ccgtggccag | 540 | |
| gggcccgccg ccatgacccc tccaaggacc tcgaaggcca ggtctcggcc gccgaggcc | 600 | |
| ggcatcaccg gcacctggta caaccagctc ggctcgacct tcatcgtgac cgcgggcgcc | 660 | |
| gacggcgccc tgaccggaac ctacgagtcg gccgtcggca acgccgagag ccgctacgtc | 720 | |
| ctgaccggtc gttacgacag cgccccggcc accgacggca gcggcaccgc cctcggttgg | 780 | |

```
acggtggcct ggaagaataa ctaccgcaac gcccactccg cgaccacgtg gagcggccag      840
tacgtcggcg gcgccgaggc gaggatcaac acccagtggc tgctgacctc cggcaccacc      900
gaggccaacg cctggaagtc cacgctggtc ggccacgaca ccttcaccaa ggtgaagccg      960
tccgccgcct ccatcgacgc ggcgaagaag gccggcgtca acaacggcaa cccgctcgac     1020
gccgttcagc agggatccct gttcacgccg ctgctcattg gctttgtggt cgcagctggc     1080
gcgatgggga tcattgtgat ggtgctctaa actagtgcct cgactgtgcc ttctagttgc     1140
cagccatctg ttgtttgccc ctcccccgtg ccttccttga ccctggaagg tgccactccc     1200
actgtccttt cctaataaaa tgaggaaatt gcatcgcatt gtctgagtag gtgtcattct     1260
attctggggg gtggggtggg gcaggacagc aagggggagg attgggaaga caatagcagg     1320
catgctgggg a                                                          1331
```

PEG-PROM MEDIATED SURFACE EXPRESSION OF AVIDIN/STREPTAVIDIN

CROSS-REFERENCE TO RELATED APPLICATIONS

This application is a U.S. national stage application under 35 U.S.C. § 371 of International Application No. PCT/US2014/040913, filed Jun. 4, 2014, which claims the benefit of U.S. Provisional Application No. 61/830,955, filed Jun. 4, 2013, which are incorporated herein by reference in their entireties.

FIELD OF THE INVENTION

The presently disclosed subject matter generally relates to genetic constructs and methods for their use in cancer imaging, cancer treatment, and combined imaging and treatment protocols. In particular, transcription of genes in the constructs is driven by cancer specific promoters.

BACKGROUND

Targeted imaging of cancer remains an important but elusive goal. Such imaging could provide early diagnosis, detection of metastasis, aid treatment planning and benefit therapeutic monitoring. By leveraging the expanding list of specific molecular characteristics of tumors and their microenvironment, molecular imaging also has the potential to generate tumor-specific reagents. But many efforts at tumor-specific imaging are fraught by nonspecific localization of the putative targeted agents, eliciting unacceptably high background noise.

While investigators use many strategies to provide tumor-specific imaging agents—largely in the service of maintaining high target-to-background ratios—they fall into two general categories, namely direct and indirect methods (Blasberg & Tjuvajev (2003) *J. Clin. Invest.* 111:1620-1629). Direct methods employ an agent that reports directly on a specific parameter, such as a receptor, transporter or enzyme concentration, usually by binding directly to the target protein. Indirect methods use a reporter transgene strategy, in analogy to the use of green fluorescent protein (GFP) in vitro, to provide a read-out on cellular processes occurring in vivo by use of an external imaging device. Molecular-genetic imaging employs an indirect technique that has enabled the visualization and quantification of the activity of a variety of gene promoters, transcription factors and key enzymes involved in disease processes and therapeutics in vivo including Gli (Zhang (2007) *Cancer Res.* 67:9389-9397), E2F1 (Uhrbom et al. (2004) *Nat. Med.* 10:1257-1260), telomerase (Kishimoto et al. (2006) *Nat. Med.* 12:1213-1219; Padmanabhan et al. (2006) *J. Nucl. Med.* 47:270-277), and several kinases, including one that has proved useful in human gene therapy trials (Freytag et al. (2007) *Mol. Ther.* 15:1016-1023; Yaghoubi et al. (2009) *Nat. Clin. Pract. Oncol.* 6:53-58). Unfortunately, these techniques have been limited by problems relating to insufficient specific localization of imaging agents and unacceptably high background noise.

Cancer therapies have also advanced considerably during the last few decades. However, they are also still hampered by nonspecific delivery of anti-tumor agents to normal cells, resulting in significant side effects for patients. This lack of specificity also results in lower efficacy of treatments due to the need for delivery of active agents in a focused manner to cancer cells alone.

The presently disclosed subject matter relates to the use of a vector comprising a unique cancer-specific promoter (Progression elevated gene-3 promoter; PEG-Prom) and a cell membrane localization signal to express avidin/streptavidin on the surface of cancer cells. The vector uniquely and specifically targets cancer cells for detection or destruction, for example by combining the vector with delivery of a therapeutic cytokine to eliminate both primary and metastatic cancer cells.

SUMMARY

The presently disclosed subject matter provides nucleic acid construct comprising a first promoter operably linked to a gene encoding avidin or streptavidin, and a second promoter operably linked to a gene encoding a therapeutic agent, wherein the first promoter is cancer-selective. In some aspects, a viral vector comprises the nucleic acid construct wherein the viral vector is selected from the group consisting of adenoviral, lentiviral, retroviral, adeno-associated viral, and herpes simplex viral. In other aspects, a nanoparticle comprises the nucleic acid construct. In still further aspects, the nanoparticle is selected from the group consisting of: a liposome, an exosome, a nanodiamond, a polyphosphazene, a dendrimer, a polyplex, a lipoplex, a polymeric nanoconjugate, a high density lipoprotein (HDL), a fluorescent super paramagnetic iron oxide nanoparticle (FSPION), a gel (e.g., chitosan or gelatin), a block copolymer micelle, and an inversion emulsion. In one aspect, the first promoter is PEG-Prom. In another aspect, the second promoter is a constitutive promoter. In further aspects, the second promoter is a cancer-selective promoter, particularly wherein the promoter is human telomerase reverse transcriptase-Prom (hTERT-Prom). In still further aspects, the therapeutic agent is selected from the group consisting of an anti-cancer agent, an apoptosis inducing agent, a tumor suppressor agent, an immune system enhancing agent, and an immunomodulatory agent, particularly wherein the therapeutic agent is an immunomodulatory cytokine, and more particularly wherein the immunomodulatory cytokine is melanoma differentiation associated gene-7/Interleukin-24 (mda-7/IL-24). In yet another aspect, cells, particularly cancer cells, comprising the nucleic acid construct are also provided.

In another aspect of the presently disclosed subject matter, a method of imaging and treating cancerous cells in a subject is provided, comprising the steps of: a) administering to the subject a nucleic acid construct comprising a first promoter operably linked to a gene encoding avidin or streptavidin, and a second promoter operably linked to a gene encoding a therapeutic agent, wherein the first promoter is cancer-selective; b) contacting the avidin or streptavidin with a biotinylated adduct comprising an imaging agent; and; and c) detecting a detectable signal from the imaging agent; wherein the gene encoding the therapeutic agent is expressed in the cancerous cells. In some aspects, detecting a detectable signal from the imaging agent is carried out via single photon emission computed tomography (SPECT) or by positron emission tomography (PET). In another aspect, the step of administering the nucleic acid construct is carried out by intravenous injection. In a further aspect, the cancerous cells are selected from the group consisting of breast cancer, melanoma, carcinoma of unknown primary (CUP), neuroblastoma, malignant glioma, cervical, colon, hepatocarcinoma, ovarian, lung, pancreatic, and prostate cancer. In some aspects, a viral vector comprises the nucleic acid construct wherein the viral vector is selected from the group consisting of adenoviral, lentiviral, retroviral, adeno-associated viral, and herpes simplex viral. In other aspects, a nanoparticle comprises the nucleic acid construct. In still further aspects, the nanoparticle is selected from the group consisting of: a liposome, an exosome, a nanodiamond, a polyphosphazene, a dendrimer, a polyplex, a lipoplex, a polymeric nanoconjugate, a high density lipoprotein (HDL), a fluorescent super paramagnetic iron oxide nanoparticle (FSPION), a gel (e.g., chitosan or gelatin), a block copolymer micelle, and an inversion emulsion. In one aspect, the first promoter is PEG-Prom. In another aspect, the second promoter is a constitutive promoter. In further aspects, the second promoter is a cancer-selective promoter, particularly wherein the promoter is hTERT-Prom. In still further aspects, the therapeutic agent is selected from the group consisting of an anti-cancer agent, an apoptosis inducing agent, a tumor suppressor agent, an immune system enhancing agent, and an immunomodulatory agent, particularly wherein the therapeutic agent is an immunomodulatory cytokine, and more particularly wherein the immunomodulatory cytokine is mda-7/IL-24.

In another aspect of the presently disclosed subject matter, a method of treating cancerous cells in a subject is provided, comprising the steps of: a) administering to the subject a nucleic acid construct comprising a first promoter operably linked to a gene encoding avidin or streptavidin, and a second promoter operably linked to a gene encoding a first therapeutic agent, wherein the first promoter is cancer-selective and wherein the gene encoding the therapeutic agent is expressed in the cancerous cells; and b) contacting the avidin or streptavidin with a biotinylated adduct comprising a second therapeutic agent. In one aspect, the step of administering the nucleic acid construct is carried out by intravenous injection. In a further aspect, the cancerous cells are selected from the group consisting of breast cancer, melanoma, carcinoma of unknown primary (CUP), neuroblastoma, malignant glioma, cervical, colon, hepatocarcinoma, ovarian, lung, pancreatic, and prostate cancer. In some aspects, a viral vector comprises the nucleic acid construct wherein the viral vector is selected from the group consisting of adenoviral, lentiviral, retroviral, adeno-associated viral, and herpes simplex viral. In other aspects, a nanoparticle comprises the nucleic acid construct. In still further aspects, the nanoparticle is selected from the group consisting of: a liposome, an exosome, a nanodiamond, a polyphosphazene, a dendrimer, a polyplex, a lipoplex, a polymeric nanoconjugate, a high density lipoprotein (HDL), a fluorescent super paramagnetic iron oxide nanoparticle (FSPION), a gel (e.g., chitosan or gelatin), a block copolymer micelle, and an inversion emulsion. In one aspect, the first promoter is PEG-Prom. In another aspect, the second promoter is a constitutive promoter. In further aspects, the second promoter is a cancer-selective promoter, particularly wherein the promoter is hTERT-Prom. In still further aspects, the first therapeutic agent and/or the second therapeutic agent are each selected from the group consisting of an anti-cancer agent, an apoptosis inducing agent, a tumor suppressor agent, an immune system enhancing agent, and an immunomodulatory agent. In other aspects, the first therapeutic agent and/or the second therapeutic agent is an immunomodulatory cytokine, particularly wherein the immunomodulatory cytokine is mda-7/IL-24.

In another aspect of the presently disclosed subject matter, a composition comprising an ultrasound targeted microbubble population is provided, wherein the microbubble population stably binds a nucleic acid construct comprising a first promoter operably linked to a gene encoding avidin or streptavidin, and a second promoter operably linked to a gene encoding a therapeutic agent, wherein the first promoter is cancer-selective.

In a further aspect, a method for delivering a nucleic acid construct to cancerous cells in a subject is provided, comprising the steps of: a) providing an ultrasound targeted microbubble population stably binding the nucleic acid construct; b) providing an ultrasound device capable of directing the microbubble population to the cancer cells; c) directing the microbubble population to the cancer cells with the ultrasound device; and d) bursting the microbubble population under conditions such that the nucleic acid construct is delivered to the cancer cells; wherein the nucleic acid construct comprises a first promoter operably linked to a gene encoding avidin or streptavidin, and a second promoter operably linked to a gene encoding a therapeutic agent, wherein the first promoter is cancer-selective.

Certain aspects of the presently disclosed subject matter having been stated hereinabove, which are addressed in whole or in part by the presently disclosed subject matter, other aspects will become evident as the description proceeds when taken in connection with the accompanying Examples and Figures as best described herein below.

BRIEF DESCRIPTION OF THE FIGURES

Figure 1:
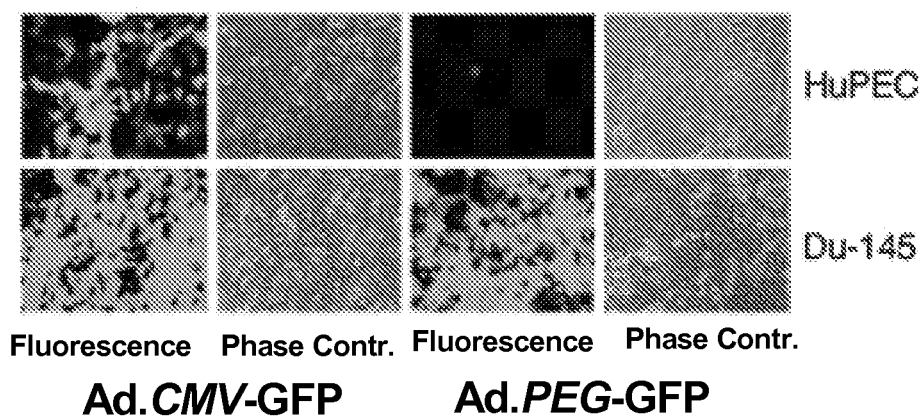
Figure 2:
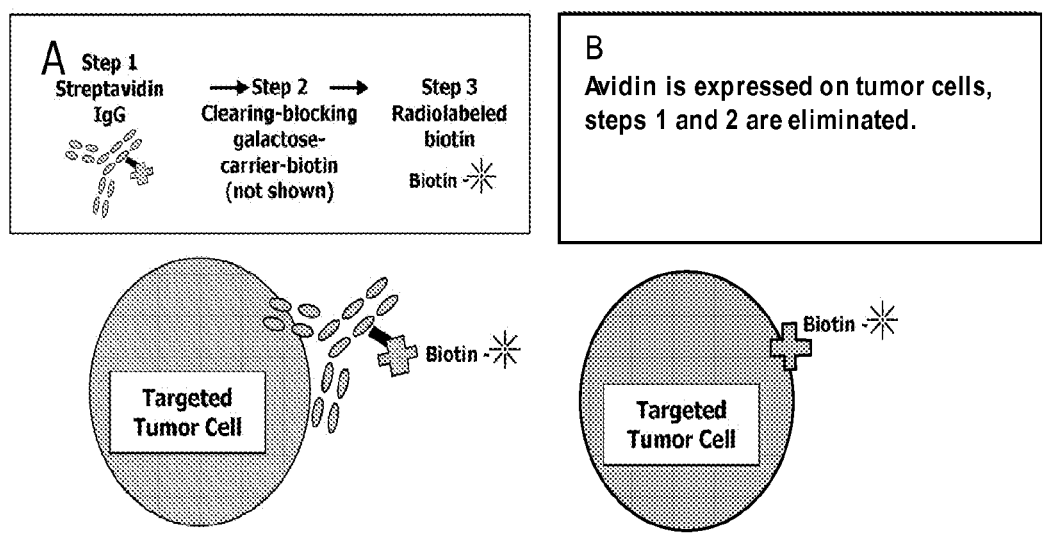
Figure 3:
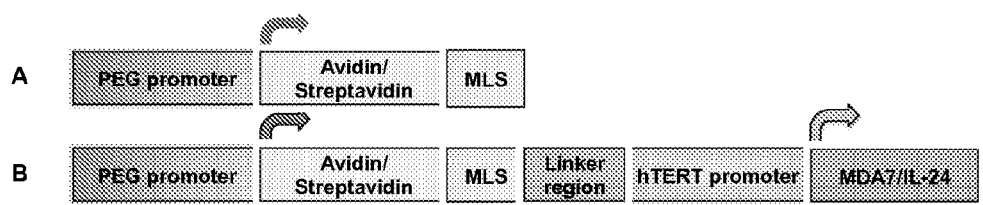
Figure 4A:
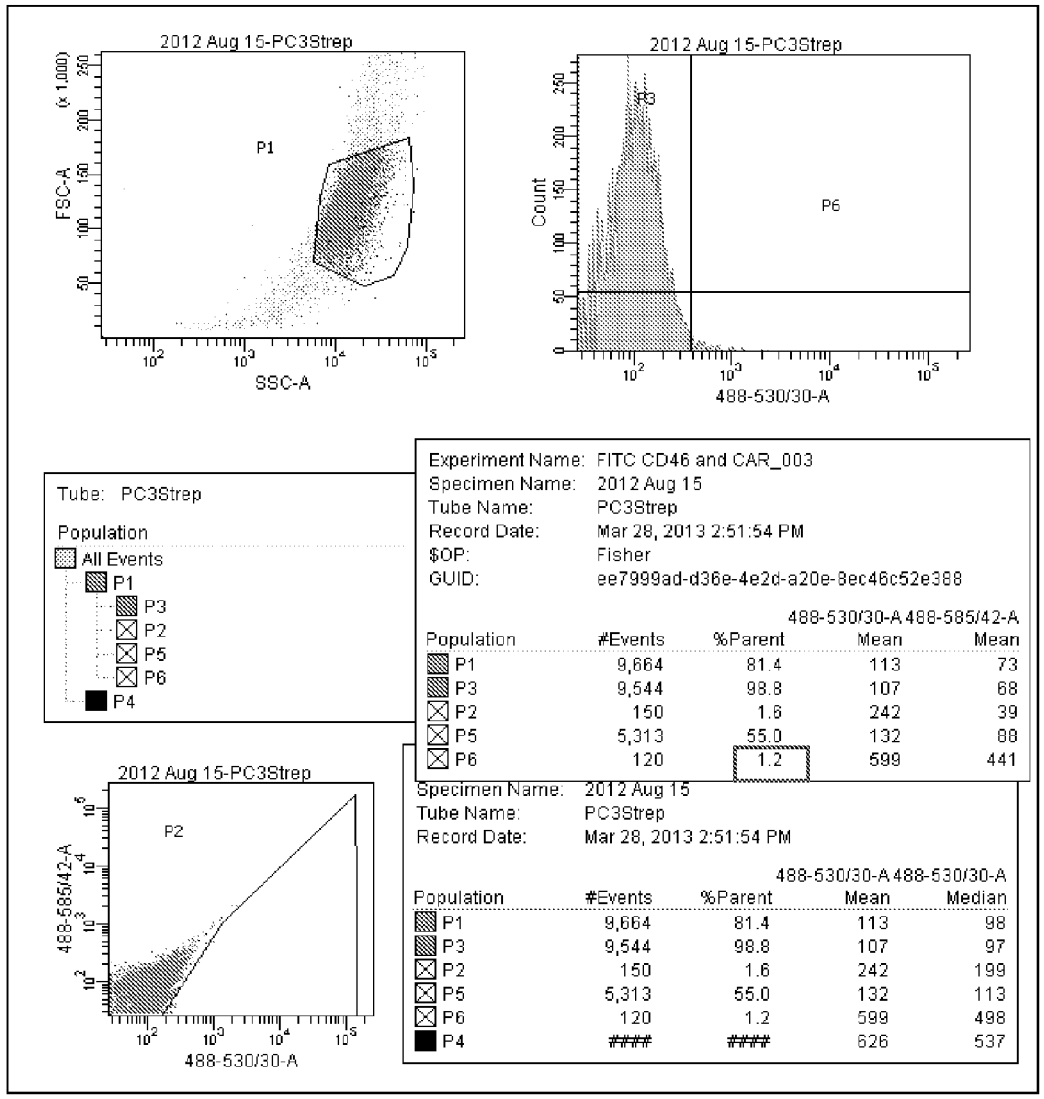
Figure 4B:
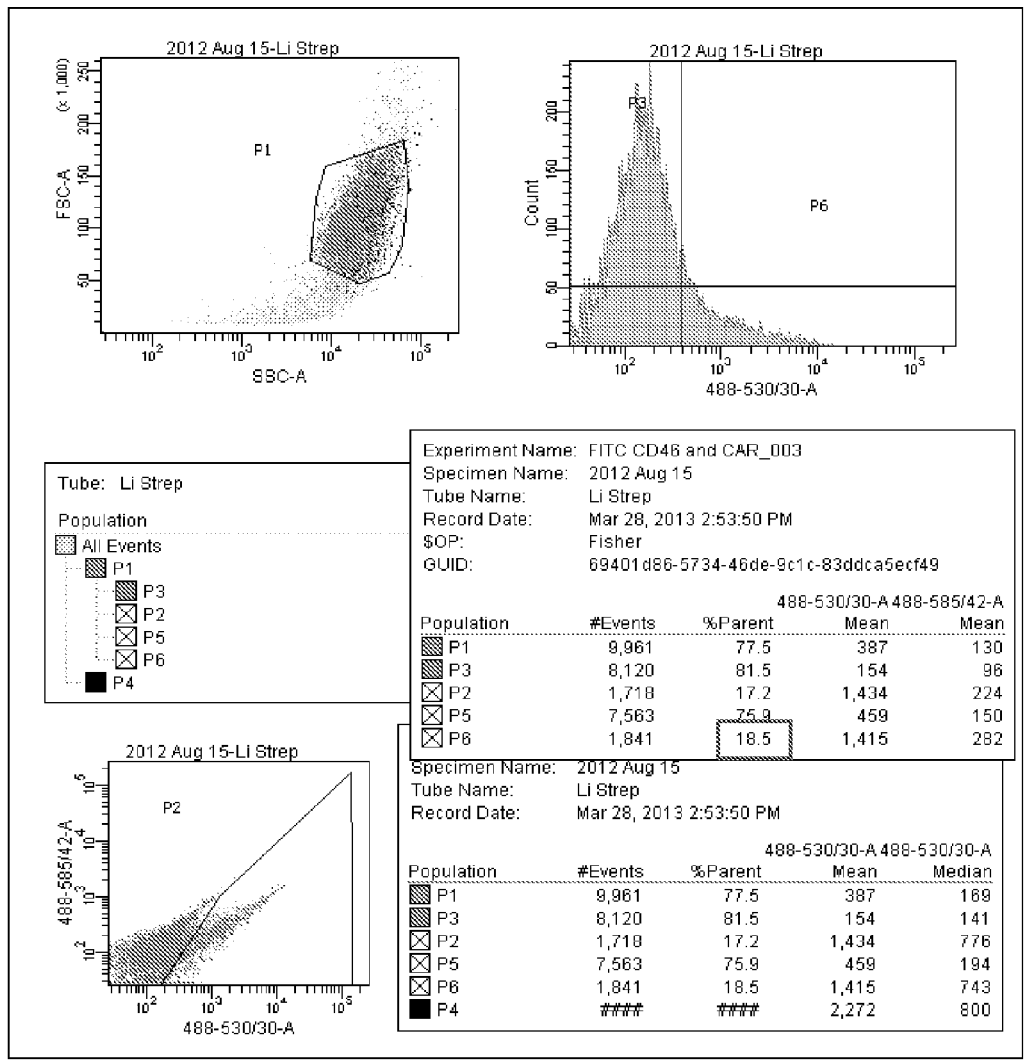

Having thus described the presently disclosed subject matter in general terms, reference will now be made to the accompanying Figures, which are not necessarily drawn to scale, and wherein:

FIG. 1 shows that PEG-Prom drives the expression of GFP in PCa cells but not in normal prostatic epithelial cells. The indicated cells were infected with either Ad.CMV-GFP or Ad.PEG-GFP and GFP expression was analyzed by immunofluorescence two days post-infection. HuPEC: primary human prostate epithelial cells; Du-145 is a PCa cell line;

FIG. 2 shows: (A) traditional two-step targeting approach; and (B) pre-targeting is unnecessary since PEG-Prom and membrane targeting sequence will place avidin (streptavidin) directly on the cell surface;

FIG. 3 shows: (A) a schematic diagram showing the PEG-Prom driven cell membrane targeted streptavidin and avidin; and (B) the same constructs with hTERT promoter-driven MDA-7/IL-24. A linker region consisting of a few random base pairs will be incorporated after the membrane localization sequence (MLS); and FIG. 4A-4B show surface expression of Streptavidin in PC-3 prostate cancer cells. PC-3 cells were transfected with c-Kit-Streptavidin and surface streptavidin expression was assessed after 48 hrs. 18.5% cells had streptavidin localized at the cell membrane.

DETAILED DESCRIPTION

The presently disclosed subject matter now will be described more fully hereinafter with reference to the accompanying Figures, in which some, but not all embodiments of the presently disclosed subject matter are shown. Like numbers refer to like elements throughout. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains having the benefit of the teachings presented in the foregoing descriptions and the associated Figures. Therefore, it is to be understood that the presently disclosed subject matter is not to be limited to the specific embodiments disclosed and that modifications and other embodiments are intended to be included within the scope of the appended claims.

Progress in systemic cancer virotherapy has previously been hampered for several reasons that include: 1) trapping of viruses in the liver; 2) clearance of viruses by the immune system; and 3) lack of true cancer-specific expression of transgenes. In addition, when using adenoviruses, the lack of sufficient Coxsackie Adenovirus Receptors (CAR) to permit viral entry into certain cancer cells has also proven problematic. The presently disclosed subject matter overcomes these problems through the use of a nucleic acid construct with a high level of specificity for target cancer cells in order to simultaneously visualize and destroy tumors and metastases (i.e., "theranostics"). The presently disclosed subject matter is also substantially less toxic than existing cancer therapies because it localizes—even through systemic delivery—the agent to the tumor and tumor only, leaving normal tissues unharmed.

The nucleic acid constructs of the presently disclosed subject matter are unique and novel in that they provides the ability to uniquely and specifically target cancer cells for detection and/or destruction. The presently disclosed subject matter comprises a unique cancer-specific promoter (PEG-Prom) to express avidin/streptavidin containing a cell membrane localization signal permitting expression on the surface of cancer cells. Once expressed on the cell surface, avidin/streptavidin can be targeted with radiolabeled biotin to image or destroy the tumor cells. The presently disclosed subject matter would also permit a dual "thernanostic" vector that could express both avidin/streptavidin and the therapeutic cytokine mda-7/IL-24, interferon-gamma or another therapeutic molecule (survivin, TRAIL, etc.) resulting in targeted killing and "bystander killing" of cancer cells.

The presently disclosed subject matter has wide applicability for the diagnosis and therapy of cancer. The three parts to this platform technology include the cancer-specific promoter, the avidin (or streptavidin gene), and the biotinylated adduct. Using the cancer-selective gene promoter PEG-Prom, avidin/streptavidin is placed on the surface of cancer cells and serves in modified two-step "pre-targeting" process, whereby once expressed on the cell surface a biotinylated adduct can be used for cancer imaging or therapy. Specifically, the adduct can be an imaging agent for positron emission tomography (PET), single photon emission computed tomography (SPECT), optical imaging, and the like, particularly through the use of fluorophores that emit in the near-infrared region of the spectrum. Alternatively, the adduct can be a radiotherapeutic or other cytotoxic or cytostatic warhead, including nanoparticles. Delivery of the gene can be virally mediated (e.g., adenovirus, lentivirus), via a suitably designed nanoparticle, or through use of ultrasound targeted microbubble destruction (UTMD) to defined regions of the body where metastatic cells may reside.

I. Genetic Constructs

The presently disclosed subject matter provides nucleic acid construct comprising a first promoter operably linked to a gene encoding avidin or streptavidin, and a second promoter operably linked to a gene encoding a therapeutic agent, wherein the first promoter is cancer-selective. In one aspect, the first promoter is PEG-Prom. In another aspect, the second promoter is a constitutive promoter. In further aspects, the second promoter is a cancer-selective promoter, particularly wherein the promoter is hTERT-Prom.

A variety of methods and systems for DNA delivery are known in the art and may be used within the compositions and methods of the presently disclosed subject matter, including without limitation lipid-based systems (e.g., cationic lipids, lipoplexes, lipid-modified polycations, emulsions, and high density lipoprotein (HDL)); organic nanoparticles (e.g., polyplexes, micelles (block and graft copolymers), and nanogels); inorganic nanoparticles (e.g., calcium phosphate particles, super paramagnetic iron oxide nanoparticles (SPIONs) and nanodiamonds); and natural vesicles (e.g., virus like particles (VLPs) and exosomes).

Vectors which comprise the nucleic acid constructs described herein are also encompassed by embodiments of the presently disclosed subject matter and include both viral and non-viral vectors. As used herein, the term "vector" refers to a nucleic acid construct designed for transduction/transfection of one or more cell types. Vectors may be, for example, "cloning vectors," which are designed for isolation, propagation and replication of inserted nucleotides, "expression vectors," which are designed for expression of a nucleotide sequence in a host cell, a "viral vector," which is designed to result in the production of a recombinant virus or virus-like particle, or "shuttle vectors," which comprise the attributes of more than one type of vector. The term "replication" means duplication of a vector.

The term "expression vector" is used interchangeably herein with the term "plasmid" and "vector" and refers to a recombinant DNA molecule containing a desired coding sequence and appropriate nucleic acid sequences necessary for expression of the operably linked coding sequence (e.g., an insert sequence that codes for a product) in a particular host cell. The term "plasmid" refers to an extrachromosomal circular DNA capable of autonomous replication in a given cell. In certain embodiments, the plasmid is designed for amplification and expression in bacteria. Plasmids can be engineered by standard molecular biology techniques. See Sambrook et al., Laboratory Manual, Cold Spring Harbor Laboratory Press, Cold Spring Harbor (1989), N.Y. Nucleic acid sequences necessary for expression in prokaryotes usually include a promoter, an operator (optional), and a ribosome binding site, often along with other sequences.

Exemplary viral vectors include but are not limited to: bacteriophages, various baculoviruses, retroviruses, and the like. Those of skill in the art are familiar with viral vectors that are used in gene therapy applications, which include but are not limited to: Herpes simplex virus vectors (Geller et al. (1988) *Science* 241:1667-1669); vaccinia virus vectors (Piccini et al. (1987) *Meth. Enzymology*, 153:545-563); cytomegalovirus vectors (Mocarski et al., in Viral Vectors, Y. Gluzman and S. H. Hughes, Eds., Cold Spring Harbor Laboratory, Cold Spring Harbor, N.Y., 1988, pp. 78-84)); Moloney murine leukemia virus vectors (Danos et al. (1988) *Proc. Natl. Acad. Sci. USA* 85:6460-6464; Blaese et al. (1995) *Science* 270:475-479; Onodera et al. (1988) *J. Virol.* 72:1769-1774; adenovirus vectors (Berkner (1988) *Biotechniques* 6:616-626; Cotten et al. (1992) *Proc. Natl. Acad. Sci. USA* 89:6094-6098; Graham et al. (1991) *Meth. Mol. Biol.* 7:109-127; Li et al. (1993) *Human Gene Therapy* 4:403-409; Zabner et al. (1994) *Nature Genetics* 6:75-83); adeno-associated virus vectors (Goldman et al. (1997) *Human Gene Therapy* 10:2261-2268; Greelish et al. (1999) *Nature Med.* 5:439-443; Wang et al. (1999) *Proc. Natl. Acad. Sci. USA* 96:3906-3910; Snyder et al. (1999) *Nature Med.* 5:64-70; Herzog et al. (1999) *Nature Med.* 5:56-63); retrovirus vectors (Donahue et al. (1998) *Nature Med.* 4:181-186; Shackleford et al. (1988) *Proc. Natl. Acad. Sci. USA* 85:9655-9659; U.S. Pat. Nos. 4,405,712, 4,650,764 and 5,252,479, and PCT Patent Publication Nos. WO 92/07573, WO 90/06997, WO 89/05345, WO 92/05266 and WO 92/14829; and lentivirus vectors (Kafri et al. (1997) *Nature Genetics* 17:314-317), as well as viruses that are replication-competent conditional to a cancer cell such as oncolytic herpes virus NV 1066 and vaccinia virus GLV-1h68, as described in U.S. Patent Application Pub. No. 2009/0311664. In particular, adenoviral vectors may be used, e.g. targeted viral vectors such as those described in U.S. Patent Application Pub. No. 2008/0213220. Accordingly, in some aspects, a viral vector comprises the nucleic acid construct wherein the viral vector is selected from the group consisting of adenoviral, lentiviral, retroviral, adeno-associated viral, and herpes simplex viral.

Exemplary non-viral vectors that may be employed include but are not limited to, for example: cosmids or plasmids; and, particularly for cloning large nucleic acid molecules, bacterial artificial chromosome vectors (BACs) and yeast artificial chromosome vectors (YACs); as well as liposomes (including targeted liposomes); cationic polymers; ligand-conjugated lipoplexes; polymer-DNA complexes; poly-L-lysine-molossin-DNA complexes; chitosan-DNA nanoparticles; polyethylenimine (PEI, e.g. branched PEI)-DNA complexes; various nanoparticles and/or nanoshells such as multifunctional nanoparticles, metallic nanoparticles or shells (e.g. positively, negatively or neutral charged gold particles, cadmium selenide, etc.); ultrasound-mediated microbubble delivery systems; various dendrimers (e.g. polyphenylene and poly(amidoamine)-based dendrimers; etc. In still further aspects, the non-viral vector is a nanoparticle is selected from the group consisting of: a liposome, an exosome, a nanodiamond, a polyphosphazene, a dendrimer, a polyplex, a lipoplex, a polymeric nanoconjugate, a high density lipoprotein (HDL), a fluorescent super paramagnetic iron oxide nanoparticle (FSPION), a gel (e.g., chitosan or gelatin), a block copolymer micelle, and an inversion emulsion. Exemplary polyplexes include, e.g., a polyethylenimine (PEI), a polypropylenimine (PPI), a poly-L-lysine (PLL), a Poly(amidoamine) (PAMAM), and a poly (2-dimethylaminoethyl methacrylate) (PDMAEMA). Exemplary lipoplexes include, e.g., 1,2-di-O-octadecenyl-3-trimethylammonium propane (DOTMA), 1,2-dioleoyl-3-trimethylammonium-propane (DOTAP), 1,2-dimyristyloxypropyl-3-dimethyl-hydroxyethyl ammonium bromide (DMRIE), 3β-[N—(N',N'-dimethylaminoethane)-carbamoyl]cholesterol hydrochloride (DC-Chol), Lipdi 67, dioctadecylaminoglycylcarboxyspermine (DOGS), and 2,3-dioleyloxy-N-[2(sperminecarboxamido) ethyl]-N,N-dimethyl-1-propanaminium trifluoroacetate (DOSPA).

Those of skill in the art will recognize that the choice of a particular vector will depend on its precise usage. Typically, one would not use a vector that integrates into the host cell genome due to the risk of insertional mutagenesis, and one should design vectors so as to avoid or minimize the occurrence of recombination within a vector's nucleic acid sequence or between vectors.

Host cells which contain the constructs and vectors of the presently disclosed subject matter are also encompassed, e.g. in vitro cells such as cultured cells, or bacterial or insect cells which are used to store, generate or manipulate the vectors, and the like. Accordingly, in yet another aspect, cells, particularly cancer cells, comprising the tripartite nucleic acid construct are also provided. The constructs and vectors may be produced using recombinant technology or by synthetic means.

The constructs of the presently disclosed subject matter include at least one transcribable element (e.g. a gene composed of sequences of nucleic acids) that is operably connected or linked to a promoter that specifically or selectively drives transcription within cancer cells.

As used herein, the term "operably linked" means that a nucleic acid sequence or protein is placed into a functional relationship with another nucleic acid sequence or protein. For example, a promoter sequence is operably linked to a coding sequence if the promoter promotes transcription of the coding sequence. As a further example, a repressor protein and a nucleic acid sequence are operably linked if the repressor protein binds to the nucleic acid sequence. Additionally, a protein may be operably linked to a first and a second nucleic acid sequence if the protein binds to the first nucleic acid sequence and so influences transcription of the second, separate nucleic acid sequence. Generally, "operably linked" means that DNA sequences being linked are contiguous, although they need not be, and that a gene and a regulatory sequence or sequences (e.g., a promoter) are connected in such a way as to permit gene expression when the appropriate molecules (e.g., transcriptional activator proteins~transcription factors~or proteins which include transcriptional activator domains) are bound to the regulatory sequence or sequences.

Expression of the transcribable element may be inducible or constitutive. Suitable cancer selective/specific promoters (and/or promoter/enhancer sequences) that may be used include but are not limited to: PEG-Prom, astrocyte elevated gene 1 (AEG-1) promoter, survivin-Prom, human telomerase reverse transcriptase (hTERT)-Prom, hypoxia-inducible promoter (HIF-1-alpha), DNA damage inducible promoters (e.g. GADD promoters), metastasis-associated promoters (metalloproteinase, collagenase, etc.), ceruloplasmin promoter (Lee et al. (2004) *Cancer Res.* 64:1788), mucin-1 promoters such as DF3/MUC1 (see U.S. Pat. No. 7,247,297), HexII promoter as described in U.S. Patent App. Pub. No. 2001/00111128; prostate-specific antigen enhancer/promoter (Rodriguez et al. (1997) *Cancer Res.* 57:2559-2563); α-fetoprotein gene promoter (Hallenbeck et al. (1999) *Hum. Gene Ther.* 10:1721-1733); the surfactant protein B gene promoter (Doronin et al. (2001) *J. Virol.* 75: 3314-3324); MUC1 promoter (Kurihara et al. (2000) *J. Clin. Investig.* 106: 763-771); H19 promoter (U.S. Pat. No. 8,034,914); promoters described in U.S. Pat. Nos. 7,816,131, 6,897,024, 7,321,030, 7,364,727; as well as derivative forms thereof.

Any promoter that is specific for driving gene expression only in cancer cells, or that is selective for driving gene expression in cancer cells, or at least in cells of a particular type of cancer (so as to treat and image e.g. prostate, colon, breast, etc. primary and metastatic cancer) may be used in the practice of the presently disclosed subject matter. By "specific for driving gene expression in cancer cells" is meant that the promoter, when operably linked to a gene, functions to promote transcription of the gene only when located within a cancerous, malignant cell, but not when located within normal, non-cancerous cells. By "selective for driving gene expression in cancer cells" is meant that the promoter, when operably linked to a gene, functions to promote transcription of the gene to a greater degree when located within a cancer cell, than when located within non-cancerous cells. For example, the promoter drives gene expression of the gene at least about 2-fold, or about 3-, 4-, 5-, 6-, 7-, 8-, 9-, or 10-fold, or even about 20-, 30-, 40-, 50-, 60-, 70-, 80-, 90- or 100-fold or more (e.g. 500- or 1000-fold) when located within a cancerous cell than when located within a non-cancerous cell, when measured using standard gene expression measuring techniques that are known to those of skill in the art.

In one embodiment, the promoter is the PEG-Prom promoter or a functional derivative thereof. This promoter is described in detail, for example, in U.S. Pat. No. 6,737,523, the complete contents of which are herein incorporated by reference. Nucleotide sequences which display homology to the PEG-Prom promoter are also encompassed for use, e.g. those which are at least about 50, 60, 70, 75, 80, 85, 90, 95, 96, 97, 98, or 99% homologous, as determined by standard nucleotide sequence comparison programs which are known in the art.

In another aspect, the second promoter is a constitutive promoter, particularly wherein the third promoter is cytomegalovirus (CMV). In a further aspect, the second promoter is a cancer-selective promoter, particularly wherein the promoter is hTERT-Prom. In a still further aspect, the therapeutic agent is selected from the group consisting of an anti-cancer agent, an apoptosis inducing agent, a tumor suppressor agent, an immune system enhancing agent, and an immunomodulatory agent, particularly wherein the therapeutic agent is an immunomodulatory cytokine, and more particularly wherein the immunomodulatory cytokine is mda-7/IL-24.

In some embodiments, the presently disclosed subject matter provides nucleic acid constructs for use in imaging cancer cells and tumors. The constructs include at least one transcribable element that functions with one or more additional molecules in a manner that creates a signal that is detectable using imaging technology. The transcribable element is operably linked to a cancer selective/specific promoter as described above, and is generally referred to as a "reporter" molecule. Reporter molecules can cause production of a detectable signal in any of several ways: they may encode a protein or polypeptide that has the property of being detectable in its own right; they may encode a protein or polypeptide that interacts with a second substance and causes the second substance to be detectable; they may encode a protein or polypeptide that sequesters a detectable substance, thereby increasing its local concentration sufficiently to render the surrounding environment (e.g. a cancer cell) detectable. If the gene product of the reporter gene interacts with another substance to generate a detectable signal, the other substance is referred to herein as a "complement" of the reporter molecule.

In yet other embodiments, the cancer-specific or cancer-selective promoters in the vectors of the presently disclosed subject matter drive transcription of a protein or antigen to be expressed on the cell surface, which can then be tagged with a suitable detectable antibody or other affinity reagent. Candidate proteins for secretion and cell surface expression include but are not limited to: β-subunit of human chorionic gonadotropin (β hCG); human α-fetoprotein (AFP); and avidin or streptavidin (SA).

In a particular embodiment, avidin or streptavadin (SA) is used as a cell surface target in the practice of the presently disclosed subject matter. The unusually high affinity of SA with biotin provides very efficient and powerful target for imaging and therapy. To bring SA to the plasma membrane of the cancer cells, SA can be fused to glycosylphosphatidylinositol (GPI)-anchored signal of human CD 14. GPI-anchoring of SA will be suitable for therapeutic applications since GPI-anchor proteins can be endocytosed to the recycling endosomes. Once expressed on the cell surface, SA can then be bound by avidin conjugates that contain a toxic or radiotoxic warhead. Toxic proteins and venoms such as ricin, abrin, *Pseudomonas* exotoxin (PE, such as PE37, PE38, and PE40), diphtheria toxin (DT), saporin, restrictocin, cholera toxin, gelonin, *Shigella* toxin, and pokeweed antiviral protein, *Bordetella pertussis* adenylate cyclase toxin, or modified toxins thereof, or other toxic agents that directly or indirectly inhibit cell growth or kill cells may be linked to avidin; as could toxic low molecular weight species, such as doxorubicin or taxol or radionuclides such as $^{125}I$, $^{131}I$, $^{111}In$, $^{177}Lu$, $^{211}At$, $^{225}Ac$, $^{213}Bi$ and $^{90}Y$; Y antiangiogenic agents such as thalidomide, angiostatin, antisense molecules, COX-2 inhibitors, integrin antagonists, endostatin, thrombospondin-1, and interferon alpha, vitaxin, celecoxib, rofecoxib; as well as chemotherapeutic agents such as: pyrimidine analogs (5-fluorouracil, floxuridine, capecitabine, gemcitabine and cytarabine) and purine analogs, folate antagonists and related inhibitors (mercaptopurine, thioguanine, pentostatin and 2-chlorodeoxyadenosine (cladribine)); antiproliferative/antimitotic agents including natural products such as vinca alkaloids (vinblastine, vincristine, and vinorelbine), microtubule disruptors such as taxane (paclitaxel, docetaxel), vincristin, vinblastin, nocodazole, epothilones and navelbine, epidipodophyllotoxins (etoposide, teniposide), DNA damaging agents (actinomycin, amsacrine, anthracyclines, bleomycin, busulfan, camptothecin, carboplatin, chlorambucil, cisplatin, cyclophosphamide, cytoxan, dactinomycin, daunorubicin, doxorubicin, epirubicin, hexamethylmelamineoxaliplatin, iphosphamide, melphalan, merchlorehtamine, mitomycin, mitoxantrone, nitrosourea, plicamycin, procarbazine, taxol, taxotere, teniposide, triethylenethiophosphoramide and etoposide (VP16)); antibiotics such as dactinomycin (actinomycin D), daunorubicin, doxorubicin (adriamycin), idarubicin, anthracyclines, mitoxantrone, bleomycins, plicamycin (mithramycin) and mitomycin; enzymes (L-asparaginase which systemically metabolizes L-asparagine and deprives cells which do not have the capacity to synthesize their own asparagine); antiplatelet agents; antiproliferative/antimitotic alkylating agents such as nitrogen mustards (mechlorethamine, cyclophosphamide and analogs, melphalan, chlorambucil), ethylenimines and methylmelamines (hexamethylmelamine and thiotepa), alkyl sulfonates-busulfan, nitrosoureas (carmustine (BCNU) and analogs, streptozocin), trazenes-dacarbazinine (DTIC); antiproliferative/antimitotic antimetabolites such as folic acid analogs (methotrexate); platinum coordination complexes (cisplatin, carboplatin), procarbazine, hydroxyurea, mitotane, aminoglutethimide; hormones, hormone analogs (estrogen, tamoxifen, goserelin, bicalutamide, nilutamide) and aromatase inhibitors (letrozole, anastrozole); anticoagulants (heparin, synthetic heparin salts and other inhibitors of thrombin); fibrinolytic agents (such as tissue plasminogen activator, streptokinase and urokinase), aspirin, dipyridamole, ticlopidine, clopidogrel, abciximab; antimigratory agents; antisecretory agents (breveldin); immunosuppressives (cyclosporine, tacrolimus (FK-506), sirolimus (rapamycin), azathioprine, mycophenolate mofetil); anti-angiogenic compounds (TNP-470, genistein) and growth factor inhibitors (vascular endothelial growth factor (VEGF) inhibitors, fibroblast growth factor (FGF) inhibitors); angiotensin receptor blocker; nitric oxide donors; anti-sense oligonucleotides; antibodies (trastuzumab, rituximab); cell cycle inhibitors and differentiation inducers (tretinoin); mTOR inhibitors, topoisomerase inhibitors (doxorubicin (adriamycin), amsacrine, camptothecin, daunorubicin, dactinomycin, eniposide, epirubicin, etoposide, idarubicin, irinotecan (CPT-11) and mitoxantrone, topotecan, irinotecan), corticosteroids (cortisone, dexamethasone, hydrocortisone, methylpednisolone, prednisone, and prenisolone); growth factor signal transduction kinase inhibitors; mitochondrial dysfunction inducers; caspase activators; and chromatin disruptors, especially those which can be conjugated to nanoparticles.

The detectable components of the system (usually a complement or substrate) used in the imaging embodiment of the presently disclosed subject matter may be labeled with any of a variety of detectable labels, examples of which are described above. In addition, especially useful detectable labels are those which are highly sensitive and can be detected non-invasively, such as the isotopes $^{124}$I, $^{123}$I, mTc, $^{18}$F, $^{86}$Y, $^{11}$C, $^{125}$I, $^{64}$Cu, $^{67}$Ga, $^{68}$Ga, $^{201}$Tl, $^{76}$Br, $^{75}$Br, $^{111}$In, $^{82}$Rb, $^{13}$N, and others.

Those of skill in the art will recognize that many different detection techniques exist which may be employed in the practice of the present presently disclosed subject matter, and that the selection of one particular technique over another generally depends on the type of signal that is produced and also the medium in which the signal is being detected, e.g. in the human body, in a laboratory animal, in cells or tissue culture, ex vivo, etc. For example, bioluminescence imaging (BLI); fluorescence imaging; magnetic resonance imaging [MRI, e.g. using lysine rich protein (LRp) as described by Gilad et al. (2007) Nature Biotechnology 25:2; or creatine kinase, tyrosinase, β-galactosidase, iron-based reporter genes such as transferring, ferritin, and MagA; low-density lipoprotein receptor-related protein (LRP; polypeptides such as poly-L-lysine, poly-L-arginine and poly-L-threonine; and others as described, e.g. by Gilad et al. (2008) J. Nucl. Med. 49(12):1905-1908); computed tomography (CT); positron emission tomography (PET); single-photon emission computed tomography (SPECT); boron neutron capture; for metals:synchrotron X-ray fluorescence (SXRF) microscopy, secondary ion mass spectrometry (SIMS), and laser ablation inductively coupled plasma mass spectrometry (LA-ICP-MS) for imaging metals; photothermal imaging (using for example, magneto-plasmonic nanoparticles, etc.

II. Diagnostic and Therapeutic Methods

In one aspect of the presently disclosed subject matter, a method of imaging and treating cancerous cells in a subject is provided, comprising the steps of: a) administering to the subject a nucleic acid construct comprising a first promoter operably linked to a gene encoding avidin or streptavidin, and a second promoter operably linked to a gene encoding a therapeutic agent, wherein the first promoter is cancer-selective; b) contacting the avidin or streptavidin with a biotinylated adduct comprising an imaging agent; and; and c) detecting a detectable signal from the imaging agent; wherein the gene encoding the therapeutic agent is expressed in the cancerous cells. In still further aspects, the therapeutic agent is selected from the group consisting of an anti-cancer agent, an apoptosis inducing agent, a tumor suppressor agent, an immune system enhancing agent, and an immunomodulatory agent, particularly wherein the therapeutic agent is an immunomodulatory cytokine, and more particularly wherein the immunomodulatory cytokine is mda-7/IL-24.

In another aspect of the presently disclosed subject matter, a method of treating cancerous cells in a subject is provided, comprising the steps of: a) administering to the subject a nucleic acid construct comprising a first promoter operably linked to a gene encoding avidin or streptavidin, and a second promoter operably linked to a gene encoding a first therapeutic agent, wherein the first promoter is cancer-selective and wherein the gene encoding the therapeutic agent is expressed in the cancerous cells; and b) contacting the avidin or streptavidin with a biotinylated adduct comprising a second therapeutic agent. In still further aspects, the first therapeutic agent and/or the second therapeutic agent are each selected from the group consisting of an anti-cancer agent, an apoptosis inducing agent, a tumor suppressor agent, an immune system enhancing agent, and an immunomodulatory agent. In other aspects, the first therapeutic agent and/or the second therapeutic agent is an immunomodulatory cytokine, particularly wherein the immunomodulatory cytokine is mda-7/IL-24.

Targeted cancer therapy may be carried out by administering the constructs as described herein to a subject in need thereof. In this embodiment, a gene encoding a therapeutic molecule, e.g. a protein or polypeptide, which is deleterious to cancer cells is operably linked to a cancer-specific promoter as described herein in a "therapeutic construct" or "therapeutic vector". The therapeutic protein may kill cancer cells (e.g. by initiating or causing apoptosis), or may slow their rate of growth (e.g. may slow their rate of proliferation), or may arrest their growth and development or otherwise damage the cancer cells in some manner, or may even render the cancer cells more sensitive to other anti-cancer agents.

Genes encoding therapeutic molecules that may be employed in the present presently disclosed subject matter include but are not limited to suicide genes, including genes encoding various enzymes; oncogenes; tumor suppressor genes; toxins; cytokines; oncostatins; TRAIL, and the like. Exemplary enzymes include, for example, thymidine kinase (TK) and various derivatives thereof; TNF-related apoptosis-inducing ligand (TRAIL), xanthine-guanine phosphoribosyltransferase (GPT); cytosine deaminase (CD); hypoxanthine phosphoribosyl transferase (HPRT); and the like. Exemplary tumor suppressor genes include neu, EGF, ras (including H, K, and N ras), p53, Retinoblastoma tumor suppressor gene (Rb), Wilm's Tumor Gene Product, Phosphotyrosine Phosphatase (PTPase), AdE1A and nm23 Suitable toxins include Pseudomonas exotoxin A and S; diphtheria toxin (DT); E. coli LT toxins, Shiga toxin, Shiga-like toxins (SLT-1, -2), ricin, abrin, supporin, gelonin, and the like. Suitable cytokines include interferons and interleukins such as interleukin 1 (IL-1), IL-2, IL-3, IL-4, IL-5, IL-6, IL-7, IL-8, IL-9, IL-10, IL-11, IL-12, IL-13, IL-14, IL-15, IL-18, β-interferon, α-interferon, γ-interferon, angiostatin, thrombospondin, endostatin, GM-CSF, G-CSF, M-CSF, METH 1, METH 2, tumor necrosis factor, TGFβ, LT and combinations thereof. Other anti-tumor agents include: GM-CSF interleukins, tumor necrosis factor (TNF); interferon-beta and virus-induced human Mx proteins; TNF alpha and TNF beta; human melanoma differentiation-associated gene-7 (mda-7), also known as interleukin-24 (IL-24), various truncated versions of mda-7/IL-24 such as M4; siRNAs and shRNAs targeting important growth regulating or oncogenes which are required by or overexpressed in cancer cells; antibodies such as antibodies that are specific or selective for attacking cancer cells; and the like.

In some embodiments, the presently disclosed subject matter provides cancer treatment protocols in which imaging of cancer cells and tumors is combined with treating the disease, i.e. with killing, destroying, slowing the growth of, attenuating the ability to divide (reproduce), or otherwise damaging the cancer cells. These protocols may be referred to herein as "theranostics" or "combined therapies" or "combination protocols", or by similar terms and phrases.

In some embodiments, the combined therapy involves administering to a cancer patient a gene construct (e.g. a plasmid) that comprises, in a single construct, both a reporter gene (for imaging) and at least one therapeutic gene of interest (for treating the disease). In this embodiment, expression of either the reporter gene or the therapeutic gene, or preferably both is mediated by a cancer cell specific or selective promoter as described herein. Preferably, two different promoters are used in this embodiment in order to prevent or lessen the chance of crossover and recombination within the construct. Alternatively, tandem translation mechanisms may be employed, for example, the insertion of one or more internal ribosomal entry site (IRES) into the construct, which permits translation of multiple mRNA transcripts from a single mRNA. In this manner, both a reporter protein/polypeptide and a protein/polypeptide that is lethal or toxic to cancer cells are selectively or specifically produced within the targeted cancer cells.

Alternatively, the polypeptides encoded by the constructs of the presently disclosed subject matter (e.g. vectors) may be genetically engineered to contain a contiguous sequence comprising two or more polypeptides of interest (e.g. a reporter and a toxic agent) with an intervening sequence that is cleavable within the cancer cell, e.g. a sequence that is enzymatically cleaved by intracellular proteases, or even that is susceptible to non-enzymatic hydrolytic cleavage mechanisms. In this case, cleavage of the intervening sequence results in production of functional polypeptides, i.e. polypeptides which are able to carry out their intended function, e.g. they are at least 50, 60, 70, 80, 90, or 100% (or possible more) as active as the protein sequences on which they are modeled or from which they are derived (e.g. a sequence that occurs in nature), when measured using standard techniques that are known to those of skill in the art.

In other embodiments of combined imaging and therapy, two different vectors may be administered, one of which is an "imaging vector or construct" as described herein, and the other of which is a "therapeutic vector or construct" as described herein.

In other embodiments of combined imaging and therapy, the genes of interest are encoded in the genome of a viral vector that is capable of transcription and/or translation of multiple mRNAs and/or the polypeptides or proteins they encode, by virtue of the properties inherent in the virus. In this embodiment, such viral vectors are genetically engineered to contain and express genes of interest (e.g. a gene required for viral replication, a reporter gene, and a therapeutic gene) under the principle control of one or more cancer specific promoters.

The presently disclosed subject matter provides compositions that comprise one or more vectors or constructs as described herein and a pharmacologically suitable carrier. The compositions are typically for systemic administration. The preparation of such compositions is known to those of skill in the art. Typically, such compositions are prepared either as liquid solutions or suspensions, or as solid forms suitable for solution in, or suspension in, liquids prior to administration. The preparation may also be emulsified. The active ingredients may be mixed with excipients, which are pharmaceutically acceptable and compatible with the active ingredients. Suitable excipients are, for example, water, saline, dextrose, glycerol, ethanol and the like, or combinations thereof. In addition, the composition may contain minor amounts of auxiliary substances such as wetting or emulsifying agents, pH buffering agents, and the like. If it is desired to administer an oral form of the composition, various thickeners, flavorings, diluents, emulsifiers, dispersing aids or binders and the like may be added. The composition of the present presently disclosed subject matter may contain any of one or more ingredients known in the art to provide the composition in a form suitable for administration. The final amount of vector in the formulations may vary. However, in general, the amount in the formulations will be from about 1-99%.

The vector compositions (or preparations) of the present presently disclosed subject matter are typically administered systemically, although this need not always be the case, as localized administration (e.g. intratumoral, or into an external orifice such as the vagina, the nasopharygeal region, the mouth; or into an internal cavity such as the thoracic cavity, the cranial cavity, the abdominal cavity, the spinal cavity, etc.) is also included. For systemic distribution of the vector, the preferred routes of administration include but are not limited to: intravenous, by injection, transdermal, via inhalation or intranasally, or via injection or intravenous administration of a cationic polymer-based vehicle (e.g. VivojetPEI®). Liposomal delivery, which when combined with targeting moieties will permit enhanced delivery.

The ultrasound-targeted microbubble-destruction technique (UTMD) may also be used to deliver imaging and theranostic agents (Dash et al. (2011) *Proc. Natl. Acad. Sci. USA*. 108(21):8785-90); hydroxyapatite-chitosan nanocomposites (Venkatesan et al. Biomaterials. 2011 May; 32(15): 3794-806); and others (Dash et al. (2011) *Discov. Med.* 11(56):46-56); and the like. Any method that is known to those of skill in the art, and which is commensurate with the type of construct that is employed, may be utilized. In addition, the compositions may be administered in conjunction with other treatment modalities known in the art, such as various chemotherapeutic agents such a Pt drugs, substances that boost the immune system, antibiotic agents, and the like; or with other detections and imaging methods (e.g. to confirm or provide improved or more detailed imaging, e.g. in conjunction with mammograms, X-rays, Pap smears, prostate specific antigen (PSA) tests, and the like.

The term "effective amount," as in "a therapeutically effective amount," of a therapeutic agent refers to the amount of the agent necessary to elicit the desired biological response. As will be appreciated by those of ordinary skill in this art, the effective amount of an agent may vary depending on such factors as the desired biological endpoint, the agent to be delivered, the composition of the pharmaceutical composition, the target tissue or cell, and the like. More particularly, the term "effective amount" refers to an amount sufficient to produce the desired effect, e.g., to reduce or ameliorate the severity, duration, progression, or onset of a disease, disorder, or condition, or one or more symptoms thereof; prevent the advancement of a disease, disorder, or condition, cause the regression of a disease, disorder, or condition; prevent the recurrence, development, onset or progression of a symptom associated with a disease, disorder, or condition, or enhance or improve the prophylactic or therapeutic effect(s) of another therapy.

Those of skill in the art will recognize that the amount of a construct or vector that is administered will vary from subject to subject, and possibly from administration to administration for the same subject, depending on a variety of factors, including but not limited to: weight, age, gender, overall state of health, the particular disease being treated, and other factors, and the amount and frequency of administration is best established by a health care professional such as a physician. Typically, optimal or effective tumorinhibiting or tumor-killing amounts are established e.g. during animal trials and during standard clinical trials. Those of skill in the art are familiar with conversion of doses e.g. from a mouse to a human, which is generally done through body surface area, as described by Freireich et al. (1966) *Cancer Chemother Rep.* 50(4):219-244).

In general, for treatment methods, the amount of a vector such as a plasmid will be in the range of from about 0.01 to about 5 mg/kg or from about 0.05 to about 1 mg/kg (e.g. about 0.1 mg/kg), and from about $10^5$ to about $10^{20}$ infectious units (Ws), or from about $10^8$ to about $10^{13}$ IUs for a viral-based vector. In general, for imaging methods, the amount of a vector will be in the range of from about 0.01 to about 5 mg/kg or from about 0.05 to about 1 mg/kg (e.g. about 0.1 mg/kg) of e.g. a plasmid, and from about $10^5$ to about $10^{20}$ infectious units (IUs), or from about $10^8$ to about $10^{13}$ IUs for a viral-based vector. For combined imaging and therapy, the amounts of a vector will be in the ranges described above. Those of skill in the art are familiar with calculating or determining the level of an imaging signal that is required for adequate detection. For example, for radiopharmaceuticals such as [$^{124}$I]FIAU, an injection on the order or from about 1 mCi to about 10 mCi, and usually about 5 mCi, (i.e. about 1 mg of material) is generally sufficient.

Further, one type of vector or more than one type of vector may be administered in a single administration, e.g. a therapy vector plus an imaging vector, or two (or more) different therapy vectors (e.g. each of which have differing modes of action so as to optimize or improve treatment outcomes), or two or more different imaging vectors, etc.

Cancer treatment may require repeated administrations of the compositions. For example, administration may be daily or every few days, (e.g. every 2, 3, 4, 5, or 6 days), or weekly, bi-weekly, or every 3-4 weeks, or monthly, or any combination of these, or alternating patterns of these. For example, a "round" of treatment (e.g. administration one a week for a month) may be followed by a period of no administration for a month, and then followed by a second round of weekly administration for a month, and so on, for any suitable time periods, as required to optimally treat the subject.

Imaging methods also may be carried out on a regular basis, especially when a subject is known or suspected to be at risk for developing cancer, due to e.g., the presence of a particular genetic mutation, family history, exposure to carcinogens, previous history of cancer, advanced age, and the like. For example, annual, semi-annual, or bi-annual, or other periodic monitoring may be considered prudent for such individuals. Alternatively, individuals with no risk factors may simply wish to be monitored as part of routine health care, in order to rule out the disease.

The subjects or patients to whom the compositions of the presently disclosed subject matter are administered are typically mammals, frequently humans, but this need not always be the case. Veterinary applications are also contemplated. Accordingly, a "subject" can include a human subject for medical purposes, such as for the treatment of an existing disease, disorder, condition or the prophylactic treatment for preventing the onset of a disease, disorder, or condition or an animal subject for medical, veterinary purposes, or developmental purposes. Suitable animal subjects include mammals including, but not limited to, primates, e.g., humans, monkeys, apes, gibbons, chimpanzees, orangutans, macaques and the like; bovines, e.g., cattle, oxen, and the like; ovines, e.g., sheep and the like; caprines, e.g., goats and the like; porcines, e.g., pigs, hogs, and the like; equines, e.g., horses, donkeys, zebras, and the like; felines, including wild and domestic cats; canines, including dogs; lagomorphs, including rabbits, hares, and the like; and rodents, including mice, rats, guinea pigs, and the like. An animal may be a transgenic animal. In some embodiments, the subject is a human including, but not limited to, fetal, neonatal, infant, juvenile, and adult subjects. Further, a "subject" can include a patient afflicted with or suspected of being afflicted with a disease, disorder, or condition. Thus, the terms "subject" and "patient" are used interchangeably herein. Subjects also include animal disease models (e.g., rats or mice used in experiments, and the like).

The constructs and methods of the presently disclosed subject matter are not specific for any one type of cancer. By "cancer" is meant malignant neoplasms in which cells divide and grow uncontrollably, forming malignant tumors, and invade nearby parts of the body. Cancer may also spread or metastasize to more distant parts of the body through the lymphatic system or bloodstream. The constructs and methods of the presently disclosed subject matter may be employed to image, diagnose, treat, monitor, etc. any type of cancer, tumor, neoplastic or tumor cells including but not limited to: osteosarcoma, ovarian carcinoma, breast carcinoma, melanoma, hepatocarcinoma, lung cancer, brain cancer, colorectal cancer, hematopoietic cell, prostate cancer, cervical carcinoma, retinoblastoma, esophageal carcinoma, bladder cancer, neuroblastoma, renal cancer, gastric cancer, pancreatic cancer, and other like.

In addition, the presently disclosed subject matter may also be applied to imaging and therapy of benign tumors, which are generally recognized as not invading nearby tissue or metastasizing, for example, moles, uterine fibroids, and the like.

III. Ultrasound Targeted Microbubble Population Compositions and Methods

In another aspect of the presently disclosed subject matter, a composition comprising an ultrasound targeted microbubble population is provided, wherein the microbubble population stably binds a nucleic acid construct comprising a first promoter operably linked to a gene encoding avidin or streptavidin, and a second promoter operably linked to a gene encoding a therapeutic agent, wherein the first promoter is cancer-selective.

In a further aspect, a method for delivering a nucleic acid construct to cancerous cells in a subject is provided, comprising the steps of: a) providing an ultrasound targeted microbubble population stably binding the nucleic acid construct; b) providing an ultrasound device capable of directing the microbubble population to the cancer cells; c) directing the microbubble population to the cancer cells with the ultrasound device; and d) bursting the microbubble population under conditions such that the nucleic acid construct is delivered to the cancer cells; wherein the nucleic acid construct comprises a first promoter operably linked to a gene encoding avidin or streptavidin, and a second promoter operably linked to a gene encoding a therapeutic agent, wherein the first promoter is cancer-selective.

As used herein, the term "microbubble" refers to any spherical arrangement of lipids creating an outer shell and an inner void space. The lipid layer may be modified to bind molecules in a stable manner.

The use of microbubbles as gene vectors utilizes destruction of DNA-loaded microbubbles by a focused ultrasound beam during their microvascular transit through the target area, resulting in localized transduction upon disruption of the microbubble shell, while sparing non-targeted areas (see U.S. Patent App. Pub. No. 2013204166). Ultrasound/Microbubble Targeted Delivery (UMTD) has been used to deliver genes to cells in vitro, and more recently, has been employed to deliver genes in vivo to treat diabetes and cardiovascular disease in experimental animal models (Chen et al. (2007) *Gene Ther.* 14:1102-1110; Fujii et al. (2009) *J. Am. Coll. Cardiol. Cardiovasc. Imaging* 2:869-879).

In some embodiments, the microbubbles are gene or molecular therapy vectors. The use of microbubbles as gene vectors has advantages over viral systems. During UMTD, intravenously injected microbubbles can be destroyed as they transit through the microcirculation of the target site where the ultrasound beam is directed, functionally achieving selective payload delivery without the need for invasive approaches such as direct intratumor injection. The lipid microbubbles we used for UMTD have no viral proteins, and can theoretically be administered repetitively. Additionally, because the microbubbles are ultrasound contrast agents, it is possible to simultaneously image microbubble transit through the tumor, thereby enabling more precise real time guidance of plasmid delivery.

As used herein, the "bursting threshold" refers to any acoustic frequency that results in the lipid shell breakdown of a microbubble population, thereby releasing the stably bound nucleic acids. Such acoustic frequencies are usually generated by an ultrasound device operating at a frequency ranging between approximately 0.25-5 MHz, preferably between approximately 0.5-2.5 MHz, but more preferably between approximately 0.75-2.0 mHz, and most preferably between 1.0-1.5 MHz. For example, a bursting threshold of UMTD microbubbles may be approximately between 1.3-1.4 MHz.

IV. General Definitions

Following long-standing patent law convention, the terms "a," "an," and "the" refer to "one or more" when used in this application, including the claims. Thus, for example, reference to "a subject" includes a plurality of subjects, unless the context clearly is to the contrary (e.g., a plurality of subjects), and so forth.

Throughout this specification and the claims, the terms "comprise," "comprises," and "comprising" are used in a non-exclusive sense, except where the context requires otherwise. Likewise, the term "include" and its grammatical variants are intended to be non-limiting, such that recitation of items in a list is not to the exclusion of other like items that can be substituted or added to the listed items.

For the purposes of this specification and appended claims, unless otherwise indicated, all numbers expressing amounts, sizes, dimensions, proportions, shapes, formulations, parameters, percentages, parameters, quantities, characteristics, and other numerical values used in the specification and claims, are to be understood as being modified in all instances by the term "about" even though the term "about" may not expressly appear with the value, amount or range. Accordingly, unless indicated to the contrary, the numerical parameters set forth in the following specification and attached claims are not and need not be exact, but may be approximate and/or larger or smaller as desired, reflecting tolerances, conversion factors, rounding off, measurement error and the like, and other factors known to those of skill in the art depending on the desired properties sought to be obtained by the presently disclosed subject matter. For example, the term "about," when referring to a value can be meant to encompass variations of, in some embodiments, ±100% in some embodiments ±50%, in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods or employ the disclosed compositions.

Further, the term "about" when used in connection with one or more numbers or numerical ranges, should be understood to refer to all such numbers, including all numbers in a range and modifies that range by extending the boundaries above and below the numerical values set forth. The recitation of numerical ranges by endpoints includes all numbers, e.g., whole integers, including fractions thereof, subsumed within that range (for example, the recitation of 1 to 5 includes 1, 2, 3, 4, and 5, as well as fractions thereof, e.g., 1.5, 2.25, 3.75, 4.1, and the like) and any range within that range.

EXAMPLES

The following Examples have been included to provide guidance to one of ordinary skill in the art for practicing representative embodiments of the presently disclosed subject matter. In light of the present disclosure and the general level of skill in the art, those of skill can appreciate that the following Examples are intended to be exemplary only and that numerous changes, modifications, and alterations can be employed without departing from the scope of the presently disclosed subject matter. The synthetic descriptions and specific examples that follow are only intended for the purposes of illustration, and are not to be construed as limiting in any manner to make compounds of the disclosure by other methods.

Example 1

The minimal promoter region of the PEG-3 gene was identified, derived from a rodent gene through subtraction hybridization, whose expression directly correlates with malignant transformation and tumor progression in rodent tumors as well as in human tumors, including different cancer cell lines and primary tumors. Based on these observations, it was hypothesized that the systemic administration of a PEG-Prom-driven imaging construct would enable tumor-specific expression of reporter genes, not only within the primary tumor, but also in associated metastases in a manner broadly applicable to tumors of different tissue origin or subtype. PEG-Prom is responsive directly to transcription factors unique to tumor cells and no homolog has been found in the human genome, which makes the use of PEG-Prom in human subjects likely to produce only minimal background signal. Previous efforts had documented that the activity of the PEG-Prom (expression of GFP driven by PEG-Prom) occurs only in human prostate carcinoma (PCa) cells (Du-145; PC-3; LNCaP) and not in normal early passage prostatic epithelial cells (HuPEC) (FIG. 1: not shown PC-3 and LNCaP).

The therapeutic utility of MDA-7/IL-24 was tested in various cancers, including PCa. Prior studies using adenovirus (Ad)-based oncolytic gene delivery strategies to induce MDA-7/IL-24 expression resulted in the complete eradication of tumors and metastases in nude mice. Ad-based gene delivery is very effective in expressing proteins in vivo. However, its immunogenicity and non-specific trapping in the liver and other sites in the body limits therapeutic applications. By using the PEI polyplex delivery vehicle, the problems of viral vectors in gene delivery are avoided, including immune reactions, off-target localization and the potential for insertional mutagenesis promoting cancer.

Using pDNA vectors, the integration rate of the extrachromosomal gene into the host genome in vivo is also negligible.

The avidin-biotin pretargeting technique reduces radiation dose to normal organs and substantially improves tumor-to-normal organ dose ratios, enabling order of magnitude increases in tumor-absorbed dose with no concomitant increase in toxicity. In the conventional implementation, a monoclonal antibody or engineered targeting molecule conjugated to streptavidin is given first (FIG. 2). After administration of a biotinylated N-acetylgalactosamine-containing "clearing agent" to remove excess circulating antibody, therapeutically radiolabeled biotin is infused. The radiolabeled biotin is ~600 times smaller than an antibody and can rapidly distribute and bind specifically to "pretargeted" streptavidin at the tumor, while unbound radiolabeled biotin is rapidly excreted in the urine (Axworthy et al. (2000) *PNAS* 97:1802-1807) The PEG-Prom-driven approach will bypass the first two steps by directly placing avidin on the surface of tumor cells. The need for an antibody-(strept)/avidin conjugate is eliminated, as is the requirement for a clearing agent. Once tumor cells have been induced to express avidin on their surface, radiolabeled biotin is administered to deliver rapidly and specifically targeted radiation to tumor cells; the biotin-avidin interaction has a dissociation constant of $10^{-6}$ nM, approximately 6 orders of magnitude stronger than the strongest antibody-antigen interaction and the strongest known non-covalent binding interaction in nature (Laitinen et al. (2007) *Trends Biotech.* 25:269-277). To target both microscopic and macroscopic tumor deposits, the following radionuclides will be investigated: $^{90}Y$ (β-particle emitter, ~2 mm range, 64 h half-life) and $^{213}Bi$ (α-particle emitter, ~80 μm range, 45.6 min half-life). The long range β-particles of $^{90}Y$ along with its longer half-life are optimal for larger, primary tumors that are typically not adjacent to highly radiosensitive normal organs while the very short range, highly potent α-particle emissions of $^{213}Bi$ and its short half-life are ideal for rapidly accessible disseminated PCa metastases in the marrow or bone.

Various novel genetic constructs are being developed permitting production of avidin (or streptavidin) under PEG-Prom or tandem production of avidin and MDA-7/IL-24 driven by hTERT-Prom, another tumor-specific promoter, to provide dual cancer-specific lethality. hTERT-Prom is required to prevent recombination with a second PEG-Prom sequence. While avidin will be expressed nearly immediately on the cell surface, MDA-7/IL-24 will require 72-96 h (to produce threshold levels that are toxic) such that a temporal aspect to the two complementary therapeutic modalities will be achieved resulting in the synergistic destruction of PCa. Reagents will be tested in vitro and in PCa models.

Development of Constructs to Express Avidin Reliably and Efficiently on the Cancer Cell Surface.

The pre-validated tumor-specific promoter PEG-Prom will be used to drive expression of avidin or streptavidin. Two major limitations for the in vivo use of the streptavidin/avidin system are its increased antigenicity and reduced ability to localize on the cell surface. To obviate these problems, PEG-Prom will be used with modified streptavidin expressing constructs. Previous studies have shown that bacterial streptavidin is spliced and expressed as a peptide with residues spanning 13-139 amino acids that lack a native bacterial recognition sequence, while retaining the biotin binding capacity with reduced antigenicity. This minimal peptide sequence will provide an entry point for generating less antigenic streptavidin. The RYD motif of streptavidin aids in surface localization yet this localization is weak and approaches are needed to enhance effective surface targeting. Based on a previous study, four different short sequences of streptavidin (lacking the native bacterial recognition sequence) will be cloned to make fusion proteins with a lipoprotein moiety. It will be confirmed that the biotin binding affinity of streptavidin is not compromised, where the 13-139 residues are critical. After the constructs containing the various modifications are developed, their surface localization, antigenicity and efficiency of expression will be assessed in vitro as well as in vivo. The proposed engineered constructs are shown in FIG. 3. The surface expression of the constructs using immunohistochemistry and $^{86}Y$-CHX-A-DTPA-biotin for imaging tumors using positron emission tomography (PET) will also be tested according to standard methods. The optimized PEI will be used for gene delivery. Antigenicity will also be determined and hematological assessment of the constructs and (strept)/avidin-producing cells in immunocompetent C57/BL-6 mice will be performed.

PCa Therapy.

$^{90}Y$- and $^{213}Bi$-CHX-A-DTPA biotin conjugates will be generated and their stability and reactivity evaluated, in vitro and in vivo. The $LD_{50}$ against avidin-expressing and non-expressing tumor cells of each will be evaluated, in vitro. The maximum tolerated dose and anti-tumor efficacy of each will also be evaluated in PCa models. Animals will first be given the optimized nanoplex, followed 24-48 h later by $^{90}Y$- or $^{213}Bi$-CHX-A-DTPA-biotin radiotherapeutic conjugates. Upon necropsy, tumor xenografts will be pathologically analyzed to evaluate cell killing. Pre-clinical studies will include macroscopic (whole-organ) biodistribution studies and for $^{213}Bi$-CHX-A-DTPA-biotin, microscopic distribution studies (by α-camera or autoradiography) for selected dose-limiting organs (e.g., kidneys or marrow). These data will allow the modeling and dosimetric analyses that will facilitate translation of pre-clinical results to an optimized human implementation. Specifically, dosimetric analysis and macro-to-micro modeling for α-particle dosimetry (Hobbs et al. (2012) *Phys. Med. Biol.* 57(13):4403-24) will enable absorbed dose-based escalation rather than administered activity based escalation in a phase I clinical trial of this approach. Tumor size will be measured with calipers, or with BLI in the case of g- or fLuc-expressing cells.

Expected Outcomes.

High and consistent avidin expression on the surface of tumor cells will be achieved. Both biotin radioconjugates will be highly effective, in vitro; due to its longer ranged emissions, cell killing with the $^{90}Y$ conjugate will be less specific to avidin expressing cells while the $^{213}Bi$ conjugate, due to the very short range emissions will be highly specific to expressing cells (i.e., the percentage difference in $LD_{50}$ against expressing vs. non-expressing cells will be much greater for the $^{213}Bi$ conjugate compared to the $^{90}Y$ conjugate). It is expected that tumor to normal tissue ratios will be 20- to 50-fold greater than typically obtained by intact antibody targeting approaches for the avidin/biotin conjugates alone. Based on the multifunction anti-cancer properties of secreted MDA-7/IL-24, selective induction of ER-stress in both primary and metastatic PCa cells is predicted resulting in apoptosis or toxic autophagy, inhibition of the tumor vasculature and stimulation of an anti-tumor response by this cytokine. The culmination of these effects will be destruction of the primary and metastatic prostate tumors.

Membrane Localizable Streptavidin/Avidin Construct Under Transcriptional Regulation of PEG-Prom Generating the Membrane Localizable Streptavidin/Avidin Construct:

The pre-validated tumor-specific promoter PEG-Prom is used to drive expression of membrane localizable avidin or streptavidin. In order to generate membrane localizable avidin and streptavidin, the membrane localization signal peptide at the N terminus and a transmembrane domain at the C terminus will be inserted from either mouse H2-K (major histocompatibility 2 K region) (Wang et al. (1996) *Ann. Transplant.* 1(3): 26-31) (GenBank Accession No. U47330) or mouse c Kit (Qui et al. (1988) *EMBO J.* 7(4):1003-11) (GenBank Accession No. Y00864) of avidin or streptavidin. Membrane localizable streptavidin using ckit and H2K signals as described above have been validated previously (Gotoh and Matsumoto (2007) *Gene* 389(2):146-53). The presently disclosed construct uses the PEG-Prom to drive transcription to obtain cancer cell-specific, membrane localization of avidin and streptavidin.

Adenovirus Constructs:

In order to generate adenoviruses, PEG-Prom, membrane localizable avidin/streptavidin and a poly A tail were introduced into the shuttle vector pE1.2 (OD 260, Inc.) as follows: The BGH poly A tail was amplified using standard PCR (polymerase chain reaction) techniques and primers as listed below and was digested with SpeI and KpnI along with the vector pE1.2. Following ligation, pE1.2-BGHpA was obtained. Next, pPEG-luc2 was cut from another construct using restriction enzymes NotI and BamHI and ligated to cut pE1.2-BGHpA to obtain pE1.2-pPEG-luc2-BGHpA. cKit and H2K transmembrane domain sequences were annealed using primers as listed below and ligated to pE1.2-pPEG-luc2-BGHpA cut with BamHI and SpeI. Finally ckit and H2K signals were obtained by annealing the primers listed below while avidin and streptavidin were amplified by PCR using the primers listed below. Avidin and Streptavidin PCR products were digested using ApaI and BamHI and the vector pE1.2-pPEG-luc2-(cKit or H2K) transmembrane domain-BGHpA was cut using SalI and BamHI (to release luc2). Annealed cKit or H2K membrane localization signals and digested avidin or streptavidin were ligated with digested pE1.2-pPEG-(cKit or H2K) transmembrane domain—BGHpA to obtain membrane localizable avidin and streptavidin constructs for adenovirus preparation. All the constructs were verified by sequencing.

TABLE 1

List of Primers.

| Name | Sequence | Sequence ID NO: |
|---|---|---|
| BGHpAF | GGACTAGTGCCTCGACTGTGCCTTC | 1 |
| BGHpAR | CGGGGTACCTCCCCAGCATGCCTGC | 2 |
| cKit transmembrane domain-F | GATCCCTGTTCACGCCGCTGCTCATTGGCTTTGTGGTCGCAGCTGGCGCGATGGGGATCATTGTGATGGTGCTCTAAA | 3 |
| cKit transmembrane domain-R | CTAGTTTAGAGCACCATCACAATGATCCCCATCGCGCCAGCTGCGACCACAAAGCCAATGAGCAGCGGCGTGAACAGG | 4 |
| H2K transmembrane domain-F | GATCCGAGCCTCCTCCATCCACTGTCTCCAACACGGTAATCATTGCTGTTCTGGTTGTCCTTGGAGCTGCAATAGTCACTGGAGCTGTGGTGGCTTAAA | 5 |
| H2K transmembrane domain-R | CTAGTTTAAGCCACCACAGCTCCAGTGACTATTGCAGCTCCAAGGACAACCAGAACAGCAATGATTACCGTGTTGGAGACAGTGGATGGAGGAGGCTCG | 6 |
| cKit membrane localization signal peptide-F | TCGACGCCGCCATGAGAGGCGCTCGCGGCGCCTGGGATCTGCTCTGCGTCCTGTTGGTCCTGCTCCGTGGCCAGGGGCC | 7 |
| cKit membrane localization signal peptide-R | CCTGGCCACGGAGCAGGACCAACAGGACGCAGAGCAGATCCCAGGCGCCGCGAGCGCCTCTCATGGCGGCG | 8 |
| H2K membrane localization signal peptide-F | TCGACGCCGCCATGGCACCCTGCATGCTGCTCCTGCTGTTGGCGGCCGCCCTGGCCCCGACTCAGACCCGCGCGGGGCC | 9 |
| H2K membrane localization signal peptide-R | CCGCGCGGGTCTGAGTCGGGGCCAGGGCGGCCGCCAACAGCAGGAGCAGCATGCAGGGTGCCATGGCGGCG | 10 |
| Avidin-F | CACGGGGCCCGCCGCCAGAAAGTGCTCGCTGAC | 11 |
| Avidin-R | ATCGCGGATCCCTCCTTCTGTGTGCGCAGGC | 12 |
| Strepavidin-F | CACGGGGCCCGCCGCCATGGACCCCTCCAAG | 13 |
| Strepavidin-R | ATCGCGGATCCCTGCTGAACGGCGTCGAG | 14 |

Mammalian Expression Constructs:

Membrane localizable avidin and streptavidin were cloned into pcDNA3.1/Hygro(+) as an intermediate step. Membrane localizable avidin and streptavidin in pE1.2 were released using restriction enzymes XbaI and KpnI and ligated to pcDNA3.1/Hygro(+) digested with NheI and KpnI. The final membrane localizable avidin and streptavidin mammalian expression constructs were made in pTracer-CMV/Bsd, a blasticidin expression plasmid. Due to the lack of appropriate restriction enzyme sites in this vector, only the cKit versions of avidin and streptavidin were generated. In order to have the expression of membrane localizable avidin and streptavidin under the PEGprom, the endogenous CMV promoter was deleted from pTracer-CMV/Bsd by cutting out the CMV promoter by digestion with SpeI. pPEG-cKit-avidin or streptavidin in pE1.2 was digested with NotI and SpeI while the vector pTracer-Bsd was digested with NotI and XbaI. Following ligation of the insert and vector, the final membrane localizable avidin and streptavidin constructs under the transcriptional regulation of PEG prom were obtained. All constructs were verified by sequencing.

Validating Surface Expression of Streptavidin in PC3 Cells:

PC3 prostate cancer cells were transiently trasnfected with cKit-streptavidin to evaluate efficacy of streptavidin to localize to the cell membrane. 48 hours after transfection, the cells were analyzed using anti streptavidin antibody by flow cytometry. 18.5% cells had streptavidin localized at the cell membrane. More positive cells might be obtained at a 72 hour time point.

TABLE 2

Vector Sequences.

| Name | Sequence | Sequence ID NO: |
|---|---|---|
| pPEG-H2K-avidin-BGHpolyA | GAAAGAGAAAGAGAATGGGACAGCATGTGACTGCCTGATGAA GTTGGCGTGCTTGCTCAAAAGTTCTGCGAGATTGACGGCTCTCT GGATTTGAGCCAAGGACACGCCTGGGAAGCCACGGTGACCTCA CAAGGCCCGGAATCTCCGCGAGAATTTCAGTGTTGTTTTCCTCT CTCCACCTTTCTCAGGGACTTCCGAAACTCCGCCTCTCCGGTGA CGTCAGCATAGCGCTGCGTCAGACTATAAACTCCCGGGTGATC GTGTTGGCGCAGATTGACTCAGTTCGCAGCTTGTGGAAGATTAC ATGCGAGACCCCGCGCGACTCCGCATCCCTTTGCCGGGACAGC CTTTGCGACAGCCCGTGAGACATCACGTCCCCGAGCCCCACGC CTGAGGGCGACATGAACGCGCTGGCCTTGAGAGCAATCCGGAC CCACGATCGCTTTTGGCAAACCGAACCGGACCGTCGACGCCGC CATGGCACCCTGCATGCTGCTCCTGCTGTTGGCGGCCGCCCTGG CCCCGACTCAGACCCGCGCGGGGCCCGCCGCCAGAAAGTGCTC GCTGACTGGGAAATGGACCAACGATCTGGGCTCCAACATGACC ATCGGGGCTGTGAACAGCAGAGGTGAATTCACAGGCACCTACA TCACAGCCGTAACAGCCACATCAAATGAGATCAAAGAGTCACC ACTGCATGGGACACAAAACACCATCAACAAGAGGACCCAGCCC ACCTTTGGCTTCACCGTCAATTGGAAGTTTTCAGAGTCCACCAC TGTCTTCACGGGCCAGTGCTTCATAGACAGGAATGGGAAGGAG GTCCTGAAGACCATGTGGCTGCTGCGGTCAAGTGTTAATGACAT TGGTGATGACTGGAAAGCTACCAGGGTCGGCATCAACATCTTC ACTCGCCTGCGCACACAGAAGGAGGGATCCGAGCCTCCTCCAT CCACTGTCTCCAACACGGTAATCATTGCTGTTCTGGTTGTCCTT GGAGCTGCAATAGTCACTGGAGCTGTGGTGGCTTAAACTAGTG CCTCGACTGTGCCTTCTAGTTGCCAGCCATCTGTTGTTTGCCCCT CCCCCGTGCCTTCCTTGACCCTGGAAGGTGCCACTCCCACTGTC CTTTCCTAATAAAATGAGGAAATTGCATCGCATTGTCTGAGTAG GTGTCATTCTATTCTGGGGGGTGGGGTGGGGCAGGACAGCAAG GGGGAGGATTGGGAAGACAATAGCAGGCATGCTGGGGA | 15 |
| pPEG-cKitsig-avidin-BGHpA | GAAAGAGAAAGAGAATGGGACAGCATGTGACTGCCTGATGAA GTTGGCGTGCTTGCTCAAAAGTTCTGCGAGATTGACGGCTCTCT GGATTTGAGCCAAGGACACGCCTGGGAAGCCACGGTGACCTCA CAAGGCCCGGAATCTCCGCGAGAATTTCAGTGTTGTTTTCCTCT CTCCACCTTTCTCAGGGACTTCCGAAACTCCGCCTCTCCGGTGA CGTCAGCATAGCGCTGCGTCAGACTATAAACTCCCGGGTGATC GTGTTGGCGCAGATTGACTCAGTTCGCAGCTTGTGGAAGATTAC ATGCGAGACCCCGCGCGACTCCGCATCCCTTTGCCGGGACAGC CTTTGCGACAGCCCGTGAGACATCACGTCCCCGAGCCCCACGC CTGAGGGCGACATGAACGCGCTGGCCTTGAGAGCAATCCGGAC CCACGATCGCTTTTGGCAAACCGAACCGGACCGTCGACGCCGC CATGAGAGGCGCTCGCGGCGCCTGGGATCTGCTCTGCGTCCTGT TGGTCCTGCTCCGTGGCCAGGGGCCCGCCGCCAGAAAGTGCTC GCTGACTGGGAAATGGACCAACGATCTGGGCTCCAACATGACC ATCGGGGCTGTGAACAGCAGAGGTGAATTCACAGGCACCTACA TCACAGCCGTAACAGCCACATCAAATGAGATCAAAGAGTCACC ACTGCATGGGACACAAAACACCATCAACAAGAGGACCCAGCCC ACCTTTGGCTTCACCGTCAATTGGAAGTTTTCAGAGTCCACCAC TGTCTTCACGGGCCAGTGCTTCATAGACAGGAATGGGAAGGAG GTCCTGAAGACCATGTGGCTGCTGCGGTCAAGTGTTAATGACAT TGGTGATGACTGGAAAGCTACCAGGGTCGGCATCAACATCTTC ACTCGCCTGCGCACACAGAAGGAGGGATCCCTGTTCACGCCGT TGCTCATTGGCTTTGTGGTCGCAGCTGGCGCGATGGGGATCATT GTGATGGTGCTCTAAACTAGTGCCTCGACTGTGCCTTCTAGTTG CCAGCCATCTGTTGTTTGCCCCTCCCCCGTGCCTTCCTTGACCCT GGAAGGTGCCACTCCCACTGTCCTTTCCTAATAAAATGAGGAA ATTGCATCGCATTGTCTGAGTAGGTGTCATTCTATTCTGGGGGG TGGGGTGGGGCAGGACAGCAAGGGGGAGGATTGGGAAGACAA TAGCAGGCATGCTGGGGA | 16 |

TABLE 2-continued

Vector Sequences.

| Name | Sequence | Sequence ID NO: |
|---|---|---|
| pPEG-H2K-streptavidin-BGHpA | GCGGCCGCGAAAGAGAAAGAGAATGGGACAGCATGTGACTGC CTGATGAAGTTGGCGTGCTTGCTCAAAAGTTCTGCGAGATTGAC GGCTCTCTGGATTTGAGCCAAGGACACGCCTGGGAAGCCACGG TGACCTCACAAGGCCCGGAATCTCCGCGAGAATTTCAGTGTTGT TTTCCTCTCTCCACCTTTCTCAGGGACTTCCGAAACTCCGCCTCT CCGGTGACGTCAGCATAGCGCTGCGTCAGACTATAAACTCCCG GGTGATCGTGTTGGCGCAGATTGACTCAGTTCGCAGCTTGTGGA AGATTACATGCGAGACCCCGCGCGACTCCGCATCCCTTTGCCGG GACAGCCTTTGCGACAGCCCGTGAGACATCACGTCCCCGAGCC CCACGCCTGAGGGCGACATGAACGCGCTGGCCTTGAGAGCAAT CCGGACCCACGATCGCTTTTGGCAAACCGAACCGGACCGTCGA CGCCGCCATGGCACCCTGCATGCTGCTCCTGCTGTTGGCGGCCG CCCTGGCCCCGACTCAGACCCGCGCGGGGCCCGCCGCCATGGA CCCCTCCAAGGACTCGAAGGCCCAGGTCTCGGCCGCCGAGGCC GGCATCACCGGCACCTGGTACAACCAGCTCGGCTCGACCTTCAT CGTGACCGCGGGCGCCGACGGCGCCCTGACCGGAACCTACGAG TCGGCCGTCGGCAACGCCGAGAGCCGCTACGTCCTGACCGGTC GTTACGACAGCGCCCCGGCCACCGACGGCAGCGGCACCGCCCT CGGTTGGACGGTGGCCTGGAAGAATAACTACCGCAACGCCCAC TCCGCGACCACGTGGAGCGGCCAGTACGTCGGCGGCGCCGAGG CGAGGATCAACACCCAGTGGCTGCTGACCTCCGGCACCACCGA GGCCAACGCCTGGAAGTCCACGCTGGTCGGCCACGACACCTTC ACCAAGGTGAAGCCGTCCGCCGCCTCCATCGACGCGGCGAAGA AGGCCGGCGTCAACAACGGCAACCCGCTCGACGCCGTTCAGCA GGGATCCGAGCCTCCTCCATCCACTGTCTCCAACACGGTAATCA TTGCTGTTCTGGTTGTCCTTGGAGCTGCAATAGTCACTGGAGCT GTGGTGGCTTAAATCAGTGCCTCGACTGTGCCTTCTAGTTGCCA GCCATCTGTTGTTTGCCCCTCCCCCGTGCCTTCCTTGACCCTGGA AGGTGCCACTCCCACTGTCCTTTCCTAATAAAATGAGGAAATTG CATCGCATTGTCTGAGTAGGTGTCATTCTATTCTGGGGGGTGGG GTGGGGCAGGACAGCAAGGGGGAGGATTGGGAAGACAATAGC AGGCATGCTGGGGA | 17 |
| pPEG-cKit-streptavidin-BGHpA | GAAAGAGAAAGAGAATGGGACAGCATGTGACTGCCTGATGAA GTTGGCGTGCTTGCTCAAAAGTTCTGCGAGATTGACGGCTCTCT GGATTTGAGCCAAGGACACGCCTGGGAAGCCACGGTGACCTCA CAAGGCCCGGAATCTCCGCGAGAATTTCAGTGTTGTTTTCCTCT CTCCACCTTTCTCAGGGACTTCCGAAACTCCGCCTCTCCGGTGA CGTCAGCATAGCGCTGCGTCAGACTATAAACTCCCGGGTGATC GTGTTGGCGCAGATTGACTCAGTTCGCAGCTTGTGGAAGATTAC ATGCGAGACCCCGCGCGACTCCGCATCCCTTTGCCGGGACAGC CTTTGCGACAGCCCGTGAGACATCACGTCCCCGAGCCCCACGC CTGAGGGCGACATGAACGCGCTGGCCTTGAGAGCAATCCGGAC CCACGATCGCTTTTGGCAAACCGAACCGGACCGTCGACGCCGC CATGAGAGGCGCTCGCGGCGCCTGGATCTGCTCTGCGTCCTGT TGGTCCTGCTCCGTGGCCAGGGGCCCGCCGCCATGGACCCCTCC AAGGACTCGAAGGCCCAGGTCTCGGCCGCCGAGGCCGGCATCA CCGGCACCTGGTACAACCAGCTCGGCTCGACCTTCATCGTGACC GCGGGCGCCGACGGCGCCCTGACCGGAACCTACGAGTCGGCCG TCGGCAACGCCGAGAGCCGCTACGTCCTGACCGGTCGTTACGA CAGCGCCCCGGCCACCGACGGCAGCGGCACCGCCCTCGGTTGG ACGGTGGCCTGGAAGAATAACTACCGCAACGCCCACTCCGCGA CCACGTGGAGCGGCCAGTACGTCGGCGGCGCCGAGGCGAGGAT CAACACCCAGTGGCTGCTGACCTCCGGCACCACCGAGGCCAAC GCCTGGAAGTCCACGCTGGTCGGCCACGACACCTTCACCAAGG TGAAGCCGTCCGCCGCCTCCATCGACGCGGCGAAGAAGGCCGG CGTCAACAACGGCAACCCGCTCGACGCCGTTCAGCAGGGATCC CTGTTCACGCCGCTGCTCATTGGCTTTGTGGTCGCAGCTGGCGC GATGGGGATCATTGTGATGGTGCTCTAAACTAGTGCCTCGACTG TGCCTTCTAGTTGCCAGCCATCTGTTGTTTGCCCCTCCCCCGTGC CTTCCTTGACCCTGGAAGGTGCCACTCCCACTGTCCTTTCCTAA TAAAATGAGGAAATTGCATCGCATTGTCTGAGTAGGTGTCATTC TATTCTGGGGGGTGGGTGGGCAGGACAGCAAGGGGGAGGA TTGGGAAGACAATAGCAGGCATGCTGGGGA | 18 |

REFERENCES

All publications, patent applications, patents, and other references mentioned in the specification are indicative of the level of those skilled in the art to which the presently disclosed subject matter pertains. All publications, patent applications, patents, and other references are herein incorporated by reference to the same extent as if each individual publication, patent application, patent, and other reference was specifically and individually indicated to be incorporated by reference. It will be understood that, although a number of patent applications, patents, and other references are referred to herein, such reference does not constitute an admission that any of these documents forms part of the common general knowledge in the art.

Although the foregoing subject matter has been described in some detail by way of illustration and example for purposes of clarity of understanding, it will be understood by those skilled in the art that certain changes and modifications can be practiced within the scope of the appended claims.

That which is claimed:

1. A nucleic acid construct comprising a first promoter operably linked to a gene encoding avidin or streptavidin comprising a membrane localization signal and a transmembrane domain, and a second promoter operably linked to a gene encoding a therapeutic agent, wherein the first promoter is cancer-selective, and wherein the construct comprises a sequence selected from the group consisting of SEQ ID NO: 15, SEQ ID NO: 16, SEQ ID NO: 17, and SEQ ID NO: 18.

2. The nucleic acid construct of claim 1, wherein the second promoter is a cancer-selective promoter.

3. The nucleic acid construct of claim 1, wherein the therapeutic agent is selected from the group consisting of an anti-cancer agent, an apoptosis inducing agent, a tumor suppressor agent, an immune system enhancing agent, and an immunomodulatory agent.

4. The nucleic acid construct of claim 1, wherein the therapeutic agent is mda-7/IL-24.

5. An isolated mammalian cell comprising the nucleic acid construct of claim 1.

6. The mammalian cell of claim 5, wherein the cell is a cancer cell.

7. A viral vector comprising the nucleic acid construct of claim 1, wherein the viral vector is selected from the group consisting of an adenoviral vector, a lentiviral vector, a retroviral vector, an adeno-associated viral vector, and a herpes simplex viral vector.

8. A nanoparticle comprising the nucleic acid construct of claim 1.

9. A method of imaging and treating cancerous cells in a subject in need thereof, comprising the steps of: administering to the subject a nucleic acid construct of claim 1, wherein the gene encoding the avidin or streptavidin and the gene encoding the therapeutic agent are expressed in cancerous cells of the subject; administering to the subject a biotinylated adduct comprising an imaging agent; and detecting a signal from the imaging agent.

10. The method of claim 9, wherein the cancerous cells are selected from the group consisting of breast cancer, melanoma, carcinoma of unknown primary (CUP), neuroblastoma, malignant glioma, cervical, colon, hepatocarcinoma, ovarian, lung, pancreatic, and prostate cancer.

11. The method of claim 9, wherein a viral vector comprises the nucleic acid construct, and wherein the viral vector is selected from the group consisting of an adenoviral vector, a lentiviral vector, a retroviral vector, an adeno-associated viral vector, and a herpes simplex viral vector.

12. The method of claim 9, wherein a nanoparticle comprises the nucleic acid construct.

13. The method of claim 9, wherein the second promoter is a cancer selective promoter.

14. The method of claim 9, wherein the therapeutic agent is selected from the group consisting of an anti-cancer agent, an apoptosis inducing agent, a tumor suppressor agent, an immune system enhancing agent, and an immunomodulatory agent.

15. The method of claim 9, wherein the therapeutic agent is mda-7/IL-24.

16. A method of treating cancerous cells in a subject, comprising the steps of: a. administering to the subject a nucleic acid construct comprising a first promoter operably linked to a gene encoding avidin or streptavidin comprising a membrane localization signal and a transmembrane domain, and a second promoter operably linked to a gene encoding a first therapeutic agent, wherein the first promoter is cancer-selective, wherein the construct comprises a sequence selected from the group consisting of SEQ ID NO: 15, SEQ ID NO: 16, SEQ ID NO: 17, and SEQ ID NO: 18, and wherein the gene encoding the therapeutic agent is expressed in the cancerous cells; and b. contacting the cancerous cells with a biotinylated adduct comprising a second therapeutic agent.

17. A composition comprising an ultrasound targeted microbubble population, wherein the microbubble population stably binds a nucleic acid construct comprising a first promoter operably linked to a gene encoding avidin or streptavidin comprising a membrane localization signal and a transmembrane domain, and a second promoter operably linked to a gene encoding a therapeutic agent, wherein the first promoter is cancer-selective, and wherein the construct comprises a sequence selected from the group consisting of SEQ ID NO: 15, SEQ ID NO: 16, SEQ ID NO: 17, and SEQ ID NO: 18.

18. A method for delivering a nucleic acid construct to cancerous cells in a subject, comprising the steps of:
 a. providing an ultrasound targeted microbubble population stably binding the nucleic acid construct of claim 1;
 b. providing an ultrasound device capable of directing the microbubble population to the cancer cells;
 c. directing the microbubble population to the cancer cells with the ultrasound device; and d. bursting the microbubble population under conditions such that the nucleic acid construct is delivered to the cancer cells;

wherein the nucleic acid construct comprises a first promoter operably linked to a gene encoding avidin or streptavidin, and a second promoter operably linked to a gene encoding a therapeutic agent, wherein the first promoter is cancer-selective.

* * * * *